United States Patent [19]
Gill et al.

[11] Patent Number: 5,804,412
[45] Date of Patent: Sep. 8, 1998

[54] NUCLEIC ACIDS ENCODING SORTING NEXINS AND METHODS OF USING SAME

[75] Inventors: Gordon N. Gill; Richard C. Kurten, both of La Jolla; Deborah L. Cadena, Encinitas, all of Calif.

[73] Assignee: The Regents of the University of California, Oakland, Calif.

[21] Appl. No.: 625,322

[22] Filed: Apr. 1, 1996

[51] Int. Cl.$^6$ .......................... C12P 21/56; C12N 15/00; C07H 17/00; C07K 14/00

[52] U.S. Cl. .................... 435/69.1; 435/325; 435/320.1; 536/23.1; 530/300; 530/350

[58] Field of Search .................................... 530/350, 351; 536/23.1; 439/69.1; 435/69.1, 320.1, 325

[56] References Cited

FOREIGN PATENT DOCUMENTS 9401548  1/1994  WIPO.

OTHER PUBLICATIONS

Gray et al. 1983 Nature 303: 722–725.
Lee et al Aug. 1995 PMAS 92: 8303–8307.
Hoffman et al. 1994 Mol. Cell Biol 14(6): 3695–3706.
Letourneur, F. and Klausner, R., "A Novel Di–Leucine Motif and a Tyrosine–Based Motif Independently Mediate Lysosomal Targeting and Endocytosis of CD3 Chains." *Cell* 69:1143–1157 (1992).
Johnson, K. and Kornfeld, S. "The Cytoplasmic Tail of the Mannose 6–Phosphate/Insulin–like Growth Factor–II Receptor has Two Signals for Lysosomal Enzyme Sorting in the Golgi." *J. Cell Biol.* 119:249–257.
Ekena, K. and Stevens, T. "The *Saccharomyces Cerevisiae* MVP1 Gene Interacts with VPS1 and is Required for Vacuolar Protein Sorting." *Mol. Cell. Biol.* 15:1671–1678 (1995).

*Primary Examiner*—Karen Cochrane Carlson
*Attorney, Agent, or Firm*—Campbell & Flores LLP

[57] ABSTRACT

The present invention provides substantially purified members of the sorting nexin (SNX) family of proteins, which are involved in down regulating the expression of cell surface receptors and directing translocation of the receptor to a lysosome in the cell, as well as active fragments of an SNX and nucleic acid molecules encoding an SNX or an active fragment thereof. In addition, the invention provides nucleotide sequences that hybridize under relatively stringent conditions to a nucleic acid molecule encoding one or more members of the SNX family of proteins. The invention further provides vectors containing a nucleic acid molecule encoding a member of the SNX family of proteins or an active fragment thereof and provides host cells containing such vectors. The present invention further provides a method of modulating the expression of a cell surface receptor by expressing a nucleic acid molecule of the invention in a cell that can express the receptor. In addition, the invention provides a method of identifying an endosomal fraction of a cell by contacting the cell or a fraction of the cell with a probe, under suitable conditions, which allow binding of the probe to an endosomal fraction, if present, such binding being detectable.

17 Claims, 2 Drawing Sheets

```
ALIGNMENT

SNX1ab    masggggcsaserlpppfpglepesegaaggsepeagdsdtegedi ftgaavvskhqspk    60
SNX2      mddr-------------------------------------------------------    4

SNX1ab    ittsllpinngskengiheeqdqepQDLFADATMELSLDSTQNNqkkvlaktIixlppqe    120
SNX2      ------------------------EDLFAEATEEMSLDGLKGNIsyprnlpIqshisll    39

SNX1ab    atnsskpqpty------------EELEEEEQEDQFDLTVGITDPEKIGDGMNAYMAYKVTT    169
SNX2      lhsapriesksmsapvifdrsrEEIEEEAENGDIFDIEIGVSDPEKVGDGMNAYMAYRVTT    99

SNX1ab    QTSLPLFRSKQFAVKRrFSDFLGLYEKLSEKHSQNGFIVPPPPEKSLIGMTKVKVGKEDS    229
SNX2      KTSLSMFSKSEFSVKR-FTDFLGLHTTLPTTYLHVIFVATSSRKSIVGMTKVKVGKEDS    158

SNX1ab    SSAEFLEKRRAALERYLQRLVMNHPTMLQDPDVREFLEKEELPRAVGTQTLSGAGLLKMFN    289
SNX2      SSHEFVEKRRAALERYLQRTMKHPTLLQDPDLRQFLESSELPRAVNTQALSGAGILRMWN    218

SNX1ab    KATDAVSKMTIKMNESDIWFEEKLQEVECEEQRLRKLHAVVETLVNHRKELALNTAQFAK    349
SNX2      KAADAVNKMTIKMNESDAWFEEKQQQFENLDQQLRKLHVSVEALVCHRKELSANTAAFAK    278

SNX1ab    SLAMLGSSEDNTALSRALSQLAEVEEKIEQLHQEQANNDFFLLAELLSDYIRLAIVRAA    409
SNX2      SAAMLGNSEDHTALSRALSQLAEVEEKIDQLHQEQAFADFYMFSELLSDYIRLTAAVKGV    338

SNX1ab    FDQRMKTWQRWQDAQATLQKKREAEARLLWANKPDKLQQAKDETLEWESRVTQERDFER    469
SNX2      FDHRMKCWQKWEDAQITLKKREAEAKMMVANKPDKITQQAKNEIREWEAKVQQGERDFEQ    398

SNX1ab    ISTYVRKEVIRFEKEKSKDFKNHVIKYLETILYSQQQLAKYWEAFLPEAKAISx     523
SNX2      ISKTIRKEVGRFEKERVKDFKTVIIKYLESLVQTQQQLIKYWEAFLPEAKAIAx    452

| EGFR-LexA Fusion | | β-Galactosidase Activity | | |
|---|---|---|---|---|
| | | Dextrose | Galactose | Fold Induction |
| 663 - 958 | | 1±0.4 (6) | 400±70 (6) | 400 |
| 647 - 1186 | | 0.6±0.3 (6) | 4±2 (6) | 6.7 |
| 647 - 957 | | 1±0.5 (6) | 500±130 (6) | 500 |
| 647 - 942 | | 0.4±0.3 (6) | 6±2 (6) | 15 |
| erbB-2 KD | | 3±0.8 (6) | 8±3 (6) | 2.7 |

FIG. 2B

```
h EGFR     FRELIIEFSKMARDPQRYLVIQGDERMHLPSPTDSNFYRALMDEEDMD  984
h erbB-2   FRELVSEFSRMARDPQRFVVIQNE-DLGPASPLDSTFYRSLLEDDDMG
neu        FRELVSEFSRMARDPQRFVVIQNE-DLGPSSPMDSTFYRSLLEDDDMG
h erbB-3   FKELANEFTRMARDPPRYLVIKRESGPGIAPGPEPHGLTNKKLEEVEL
li erbB-4  FKELAAEFSRMARDPQRYLVIQGDDRMKLPSPNDSKFFQNLLDEEDLE
```

NUCLEIC ACIDS ENCODING SORTING NEXINS AND METHODS OF USING SAME

This work was supported by grants F32DK08666 and CA58689 awarded by the National Institutes of Health. The United States Government has certain rights in this invention.

BACKGROUND OF THE INVENTION

1. Field of the Invention

This invention relates generally to the fields of molecular biology and molecular medicine and more specifically to proteins that regulate the expression of growth factor receptors on the surface of a cell.

2. Background Information

The human body contains various different types of cells, including, for example, epithelial cells, muscle cells and liver cells. These cell types, in combination with other cells such as endothelial cells, which form blood vessels, are organized into various tissues and organs such as skin, muscle and liver.

Under normal conditions, cells such as epithelial cells, which comprise, for example, the epidermal layer of skin can have a relatively short life span. As a result, cells that die must be replaced by new cells. In the skin, for example, the outer epidermal layer is continually sloughed off, while the basal layer of cells continually divide such that the loss of cells from the surface of the skin is balanced by the newly formed cells in the basal layer.

Epithelial cells also comprise the milk producing ductal cells in breast. In the breast, a significant amount of epithelial cell growth and division occurs early during development and again during adolescence, then minimal growth and division of these cells occurs unless pregnancy occurs. If pregnancy occurs, growth and division of the ductal epithelial cells is stimulated, resulting in an increase in the ductal tissue. Following birth, milk is produced for a period of time by the ductal epithelial cells, then the ductal epithelial tissue breaks down and the cells enter a resting state similar to the pre-pregnancy state. This resting state is maintained until pregnancy again occurs or until changes associated with aging occur.

Regulated growth and division normally occurs in all cells, including, for example, the cells of the nervous system. In the nervous system, nerve cells generally cease dividing shortly after birth. However, supporting and interacting glial cells continue to proliferate throughout life. Thus, different cells in the nervous system are regulated selectively.

The regulation of cell growth and division is tightly controlled by various intracellular and extracellular factors, including, for example, growth factors and hormones. Growth and division of epithelial cells, for example, is regulated, in part, by epidermal growth factor (EGF), which binds to a specific epithelial cell surface receptor, the EGF receptor (EGFR). As a result of EGF binding to the EGFR, a growth signal is transmitted into the cell. Similarly, growth and division of glial cells in the nervous system are regulated, in part, through EGF binding to EGFR on these cells.

Under normal conditions, expression of the EGFR on a cell is tightly regulated so as to control cell growth. For example, expression of the EGFR on the surface of an epithelial cell is regulated such that, upon binding of EGF, a signal is transduced into the cell resulting in stimulation of cell growth and division. In due course, however, the EGFR-EGF complex is transported from the cell surface into lysosomes, where it is degraded, thus terminating the signal for cell growth.

In some cases, cells can produce a defective growth factor receptor, which can lead to unregulated cell growth and division and can result in the development of a cancer. For example, in some breast cancers, the breast epithelial cells express an EGFR-like receptor, erbB-2, which transmits a prolonged growth signal as compared to the signal transmitted by the normal EGFR. Breast cancer patients that have high cell surface expression of erbB-2 have a relatively poor prognosis for treatment and survival as compared to patients that do not express erb-B2. Similarly, high cell surface expression of EGFR in breast or in glial cell-derived brain cancer correlates to a poor patient outcome.

The relationship of cell surface receptor expression and cell growth and division suggests that a method of down regulating the expression, for example, of a cell surface receptor such as EGFR or erbB-2 can be useful for modulating the unregulated growth of breast cancer cells expressing EGFR or erbB-2, respectively. The ability to regulate such aberrant cell growth would provide a therapeutic advantage for treating a breast cancer patient. Unfortunately, the cellular factors involved in down regulating the expression of cell surface receptors have not yet been described. Thus, a need exists to identify the proteins involved in down regulating the cell surface expression of growth factor cell surface receptors. The present invention satisfies this need and provides additional advantages.

SUMMARY OF THE INVENTION

The present invention provides members of the sorting nexin (SNX) family of proteins, which are involved in down regulating the expression of cell surface receptors and directing translocation of the receptors to a lysosome. An SNX of the invention is exemplified by human SNX1 having the amino acid sequence shown as SEQ ID NO: 2. As disclosed herein, SNX1 binds the EGFR and directs translocation of the receptor to a lysosome in the cell, thereby down regulating cell surface expression of the receptor. An SNX of the invention also is exemplified by human SNX2, which has the amino acid sequence shown as SEQ ID NO: 4 and shares substantial sequence identity with SNX1. Also provided are active fragments of an SNX protein and antibodies that specifically bind to one or more members of the SNX family of proteins.

The invention also provides a nucleic acid molecule encoding an SNX protein. For example, the invention provides a nucleic acid molecule encoding human SNX1 (SEQ ID NO: 1) and a nucleic acid molecule encoding human SNX2 (SEQ ID NO: 3). In addition, the invention provides nucleotide sequences that hybridize under relatively stringent conditions to a nucleic acid molecule encoding a member of the SNX family of proteins. The invention further provides vectors containing a nucleic acid molecule encoding a member of the SNX family of proteins or a portion thereof and provides host cells containing such vectors.

The present invention also provides a method of modulating the expression of a cell surface receptor by expressing a nucleic acid molecule of the invention in a cell that can express the receptor. In addition, the invention provides a method of identifying an endosomal fraction of a cell by contacting the cell or a fraction of the cell with a probe such as an SNX polypeptide, an active fragment thereof, an anti-SNX antibody or a peptide having a lysosomal targeting code, under suitable conditions, which allow binding of the probe to an endosomal fraction, if present, such binding being detectable.

BRIEF DESCRIPTION OF THE DRAWINGS

FIG. 1 shows an alignment of the amino acid sequences of human SNX1 (SEQ ID NO: 2), which was deduced from the nucleic acid molecule shown as SEQ ID NO: 1, and human SNX2 (SEQ ID NO: 4), which was deduced from the nucleic acid molecule shown as SEQ ID NO: 3. Alignment of SNX1 and SNX2 peptide sequences was generated using the MACAW program (Altschul and Lipman, *Proteins: Structure, function and Genetics* 9:180–190 (1991)). Identical residues in the alignment are shaded. Uppercase residues represent statistically significant blocks of sequence shared by SNX1 and SNX2. Lowercase residues represent divergent sequences, where the alignment is not significant. Dashes represent gaps inserted to maintain alignment of the sequences. The membrane trafficking domain is underlined and the receptor binding domain is double underlined. Although the methionine at amino acid 1 in SNX2 (SEQ ID NO: 4), which is the first methionine present in the amino acid sequence deduced from SEQ ID NO: 3, is shown as the first amino acid, the methionine at position 93 may be the first amino acid in SNX2 in vivo (see Example II).

FIGS. 2A and 2B illustrate domains of EGFR and EGFR-like proteins that can interact with an SNX.

FIG. 2A shows the EGFR constructs used in a two hybrid assay to identify regions of the EGFR that bind SNX1. Numbers to the left of the constructs indicate the amino acid positions of the EGFR. "erbB-2 KD" indicates the rat erbB-2 tyrosine kinase domain. The ability of the various EGFR constructs to bind SNX1 is indicated by the amount of β-galactosidase (β-gal) activity induced by galactose as compared to dextrose (control). β-gal activity is expressed as ($OD_{420}/OD_{600}$/min ×1000) ±the standard deviation; number of samples are shown in parentheses.

FIG. 2B provides an amino acid comparison of erbB family members in the region containing the EGFR tetrapeptide lysosomal targeting code (underlined). Residues that are identical between 3 of the 4 family members are indicated by bold type. "neu" indicates rat neu, which is the rat homolog of human erbB-2.

DETAILED DESCRIPTION OF THE INVENTION

The present invention provides substantially purified members of the sorting nexin ("SNX") family of proteins, which can bind to and down regulate the expression of a cell surface receptor and direct translocation of the receptor to a lysosome. An SNX of the invention is exemplified by human SNX1 having the amino acid sequence shown as SEQ ID NO: 2 (see FIG. 1), which was deduced from the nucleic acid molecule shown as SEQ ID NO: 1 (GenBank Accession No. U53225). As disclosed herein, SNX1 binds the human EGFR and directs translocation of the receptor to a lysosome in the cell. A member of the SNX family of proteins also is exemplified by SNX2 having the amino acid sequence shown as SEQ ID NO: 4 (FIG. 1).

As used herein, the term "substantially purified," when used in reference to an SNX protein, means that the SNX is in a form that is relatively free from contaminating lipids, proteins, nucleic acids or other cellular material normally associated with a protein in a cell. A substantially purified SNX protein can be obtained, for example, by expressing a nucleic acid sequence encoding the SNX or by using well known methods of biochemical purification based on the disclosed characteristics of an SNX.

The members of the SNX family of proteins are characterized in that each member of the family contains a domain that has substantially the amino acid sequence of the SNX1 membrane trafficking domain, which is involved in targeting a bound receptor to a lysosome (see Example III). As used herein, the term "substantially the amino acid sequence," when used in reference to the membrane trafficking domain of a member of the SNX family of proteins, means an amino acid sequence having at least 50% sequence identity with amino acids 214 to 265 of SNX1, which defines the membrane trafficking domain of SNX1 (SEQ ID NO: 2). For example, the membrane trafficking domain of SNX2, which is present at amino acids 143 to 194 of SEQ ID NO: 4 (see FIG. 1), shares 86.5% amino acid sequence identity with the membrane trafficking domain of SNX1, thus identifying SNX2 as a member of the SNX family of proteins. In comparison, the corresponding amino acid sequence in the yeast MVP1 protein has only about 40% sequence identity (see below).

It should be recognized that the sequence homology among members of the SNX family of proteins, particularly the sequence homology within the membrane trafficking domain, is considerably greater than the sequence identity, where the sequence homology includes amino acids that are identical as well as those representing a conservative amino acid substitution. For example, the amino acid sequence identity of the membrane trafficking domains of SNX1 and SNX2 is 86.5%, whereas the sequence homology is 90.4%. In view of this high level of sequence conservation, the skilled artisan would recognize that a probe designed to interact with the membrane trafficking domain of an SNX, or with a nucleic acid sequence encoding this domain, can be particularly useful for identifying related members of the SNX family of proteins.

Conservative amino acid substitutions are well known in the art and include, for example, the substitution of one acidic amino acid such as Glu for another acidic amino acid such as Asp, of one hydrophobic amino acid such as Leu for another hydrophobic amino acid such as Ile or other such conservative change known in the art. The presence of conservative amino acid changes are particularly evident in comparing the entire amino acid sequences of SNX1 and SNX2. For example, SNX2 shares 68.8% sequence identity with SNX1 and, when conservative amino acid substitutions are considered, shares 82.6% sequence homology with SNX1.

In addition to the high level of sequence identity and homology shared among the membrane trafficking domains of SNX1 and SNX2, high levels of identity and homology are shared in the receptor binding domains. Thus, the EGFR binding domain of SNX1 (amino acids 465–522; SEQ ID NO: 2) shares 72.4% sequence identity and 86.2% sequence homology with the corresponding domain of SNX2 (amino acids 394 to 452; SEQ ID NO: 4). This conserved sequence homology among the receptor binding domains of SNX1 and SNX2 indicates that SNX2 also may bind the EGFR or an EGFR-like receptor.

The overall structural similarities of SNX1 and SNX2 indicate that these proteins constitute two members of a family of SNX proteins, which are characterized by the ability to bind a cell surface receptor and direct translocation of the receptor to a lysosome in the cell. It is recognized, however, that individual members of the SNX family of proteins can be distinguished, in part, by the receptor to which the SNX binds. For example, SNX1 binds to and down regulates expression of the EGFR, but not, for example, the erbB-2 receptor, whereas another SNX can be involved in down regulating erbB-2 receptor expression.

As used herein, the term "down regulate," when used in reference to the expression of a cell surface receptor, means that the receptor is internalized from the cell surface into the cell. Where such down regulation is due to binding of the receptor by an SNX, the receptor further is transported to a lysosome such that degradation of the receptor occurs. Methods for identifying such down regulation of expression of a cell surface receptor are disclosed in Example III or otherwise known in the art.

Reference is made herein to various domains or sequences present in an SNX or a cell surface receptor. The term "membrane trafficking domain" is used herein to mean a peptide portion of an SNX that has at least about 50% sequence identity with amino acids 214 to 265 of SNX1 (SEQ ID NO: 2), which is involved in directing translocation of a cell surface receptor to a lysosome. A membrane trafficking domain is exemplified by amino acids 214 to 265 of SNX1 (SEQ ID NO: 2) and by amino acids 143 to 194 in SNX2 (SEQ ID NO: 4; see FIG. 1). In view of the characteristics of a membrane trafficking domain as defined herein, the skilled artisan can readily determine that a putative membrane trafficking domain is, in fact, a membrane trafficking domain by identifying the appropriate sequence identity, then examining the domain using, for example, the methods disclosed in Example III.

The term "receptor binding domain" is used herein to mean a peptide portion of an SNX that associates with a particular cell surface receptor. A receptor binding domain is exemplified by the EGFR binding domain of SNX1 (amino acids 465–522; SEQ ID NO: 2). In general, receptor binding domains in different members of the SNX family of proteins need not necessarily share substantial sequence identity or sequence homology. However, the receptor binding domain of SNX2 shares 72.4% sequence identity and 86.2% sequence homology with the EGFR binding domain of SNX1, indicating, for example, that SNX2 may bind EGFR or an EGFR-like receptor. Upon identifying a putative SNX protein, the skilled artisan would recognize that the particular receptor bound by the SNX can be identified using, for example, the λgt11 expression cloning method or the two hybrid assay (see Example III; see, also, Vogt and Verma, *Meth. Enzymol.*, Vol. 254 (Academic Press 1995), which is incorporated herein by reference; see Chaps. 15 and 16). Such methods can be used, for example, to identify a receptor bound by SNX2. Nucleic acid molecules encoding various cell surface receptors are known in the art and available, for example, from GenBank or from the American Type Culture Collection.

The term "lysosomal targeting code" is used herein to mean an amino acid sequence that is present in a cell surface receptor and required for SNX binding to the receptor. A lysosomal targeting code can be based on a leu-leu motif or a tyrosine motif (Letourneur and Klausner, *Cell* 1143–1157 (1992); Johnson and Kornfeld, *J. Cell Biol.* 119:249–257 (1992), each of which is incorporated herein by reference. For example, the consensus tyrosine motif based lysosomal targeting code, Y-X-X-Hyd (where "Y" is tyrosine, "X" is any amino acid, and "Hyd" indicates a hydrophobic amino acid) is present in four major lysosomal proteins (Guarnieri et al., *J. Biol. Chem.*, 268:1941–1946 (1993)).

The EGFR contains the sequence YLVI (see FIG. 2B), which fits within the consensus tyrosine motif based lysosomal targeting code. As disclosed herein, deletion of EGFR amino acids 942 to 957, including the YLVI sequence, abolished SNX1 binding (see Example III and FIG. 2B). In addition, SNX1 does not bind the erbB-2 receptor, which contains the sequence FVVI in the position corresponding to YLVI in the EGFR (FIG. 2B). These results indicate that the lysosomal targeting code is required for SNX binding to a receptor that, upon down regulation from the cell surface, is sorted to a lysosome. These results further indicate that a domain of a cell surface receptor that contains the lysosomal targeting code can be used as a probe to identify the presence of an SNX in a sample or to identify additional members of the SNX family of proteins.

Ligand-activated growth factor and nutrient receptors are internalized from the cell surface via clathrin coated pits and are colocalized in clathrin coated vesicles. Upon internalization, the clathrin is removed from the vesicle to form an early endosome. At this point, one of two events occurs, depending on the particular ligand-receptor complex present in the early endosome. In one case, exemplified by the transferrin receptor complexed with an iron containing protein, the receptor-ligand complex is dissociated in the late endosome, the ligand is released to the cytosol or transported to another compartment in the cell, and the receptor is recycled to the cell surface. In the other case, exemplified by the EGFR, the receptor-ligand complex is transported from the early endosome, through a late endosome, to a lysosome, where the receptor and ligand are degraded.

The task of sorting receptors such as EGFR, which are destined for lysosomal degradation, from receptors such as the transferrin receptor, which is recycled, is accomplished in the early endosome. Since the sorting, for example, of an internalized EGFR from the late endosome to a lysosome is a saturable phenomenon, the existence of specific sorting proteins was postulated. The recognition that lysosomal targeting codes are involved in the endocytic and exocytic pathways that direct proteins to a lysosome following endocytosis of the protein from the cell surface or upon release of the protein from the Golgi apparatus provided further support for the existence of specific sorting proteins (see FIG. 2B; see, also, Letourneur and Klausner, supra, 1992; Johnson and Kornfeld, supra, 1992). Prior to the present disclosure, however, a protein involved in sorting a cell surface receptor that is to be recycled from a receptor destined to degradation in a lysosome was not described.

In yeast, more than fifty gene products are involved in sorting precursor carboxypeptidase Y (pCPY) to the vacuole, which is the yeast equivalent of a mammalian cell lysosome. For example, the yeast pCPY receptor, Vps10p, cycles between the trans-Golgi network and vacuolar compartments, delivering pCPY to the vacuole. This cycling of Vps10p requires the activity of a high molecular weight GTPase, Vps1p, which shares substantial similarity to the mammalian protein, dynamin, which is required for coated vesicle budding.

Another yeast protein, MVP1, was isolated as a multicopy suppressor of VPS1 mutants deficient in CpY receptor trafficking and found to colocalize with Vps1p to Golgi membranes (Ekena and Stevens, *Mol. Cell. Biol.* 15:1671–1678 (1995)). As disclosed herein, the SNX family of proteins contains a membrane trafficking domain, exemplified by amino acids 214 to 265 of SNX1 (SEQ ID NO: 2; see FIG. 1), that is homologous to a region of Mvp1. However, this region of MVP1 shares only about 40% sequence identity to amino acids 214 to 265 of SNX1 and, therefore, is distinguished from the present invention.

A member of the SNX family of proteins is exemplified by SNX1, which binds the EGFR, down regulates its expression from the surface of a cell and directs its translocation to a lysosome in the cell. The EGFR is a cell surface receptor containing 1186 amino acids, including an amino terminal extracellular domain, which contains the EGF binding site; a transmembrane domain; and a carboxy terminal intracellular domain. The intracellular domain of the EGFR consists of amino acid residues 647 to 1186, including the core tyrosine kinase domain (residues 663–958) and a lysosomal targeting code (amino acids 954–957; YLVI; SEQ ID NO: 5). The tyrosine kinase domain of the EGFR can phosphorylate various intracellular proteins and also autophosphorylates itself. Through these phosphorylation events, the extracellular growth factor signal is transduced into the cell, resulting, in the case of EGF, for example, in signaling an epithelial cell to enter a cycle of cell growth and division.

EGF binding to the EGFR and autophosphorylation of the EGFR also results in a conformational change in the EGFR such that SNX1 can bind to the receptor. Thus, EGF binding to the EGFR acts not only as a signal for cell growth, but also as a signal for SNX binding, which down regulates expression of the EGF-EGFR complex from the cell surface to a lysosome, where the complex is degraded, thereby terminating the EGF induced growth signal.

The EGFR is encoded by the erbB-1 gene and is a member of a family of EGFR-like proteins. Other growth factor receptors such as the platelet derived growth factor (PDGF) receptor (PDGFR) and the insulin receptor also contain a tyrosine kinase domain that is activated upon binding of the respective growth factor to its receptor. Other cell surface receptors, including, for example, the β-adrenergic receptor, are G protein coupled receptors that transduce an extracellular signal to the nucleus through the second messenger, cyclic AMP. Similar to the EGFR, the PDGFR, insulin receptor and β-adrenergic receptor are internalized by the cell upon binding their respective ligands and translocated to a lysosome, where the ligand-receptor complex is degraded and signal transduction is terminated. In addition, binding of a cytokine to its specific cytokine receptor results in internalization of the complex and translocation to a lysosome for degradation. One or more members of the SNX family of proteins can be involved in sorting these different receptor-ligand complexes to a lysosome.

In some cases, cells express an aberrant cell surface receptor such that the regulation of signal transduction is compromised. For example, the viral erbB oncogene, v-erbB, encodes an EGFR-like receptor that lacks an extracellular domain and, therefore, cannot bind EGF (Downward et al., Nature, 307:521–527 (1984)). Nevertheless, this mutant EGFR-like receptor is constitutively active, resulting in unregulated transmission of a growth signal to a cell expressing the receptor. In addition, a valine to glutamic acid mutation in the transmembrane domain coding sequence of the rat neu gene, which is a homolog of the human erbB-2 gene, results in the formation of a mutant EGF-like receptor containing a single amino acid change in the transmembrane domain. The mutant neu receptor also is constitutively active and results in unregulated growth of a cell expressing the receptor (Coussens et al., Science 230:1132–1139 (1985); Bargmann et al., Cell 45:649–657 (1986)).

As disclosed herein, SNX1 possesses the binding specificity and functional properties expected of a sorting nexin. Over-expression of SNX1 in stably transfected CV-1 cells down regulated the expression of endogenous EGFR, but not of the endogenous erbB-2 receptor or PDGFR (see Example III.B.). The carboxy terminal domain of SNX1 (amino acids 465–522) recognizes an amino acid sequence containing the EGFR lysosomal targeting code, which is required for SNX1 binding to EGFR and down regulation of the receptor (Example III.A.), whereas the presence of FVVI (SEQ ID NO: 6) in erbB-2/neu in the position corresponding to YLVI (SEQ ID NO: 5) in EGFR results in the failure of SNX1 to bind erbB-2.

In general, binding of an SNX to a receptor occurs subsequent to the binding of a particular ligand to the receptor or upon activation of the receptor. For example, SNX1 failed to bind the full length EGFR in an in vitro assay, but was able to bind to a carboxy terminal truncated EGFR (Example II). These results indicate that the EGFR must undergo a conformational change to expose a cryptic SNX1 binding site. Such a conformational change occurs upon binding of EGF to the EGFR, which results in autophosphorylation of the EGFR and dimerization of the activated receptors. In contrast, mutant growth factor receptors such as the receptor encoded by the viral erbB oncogene can be constitutively active even though the receptor cannot bind a growth factor. Expression in a cell of an SNX that can bind such a constitutively active growth factor receptor can be useful for down regulating expression of the mutant receptor, thus terminating the unregulated growth signal.

The present invention also provides an active fragment of an SNX protein. As used herein, the term "active fragment," when used in reference to an SNX, means a peptide portion of an SNX having an activity that is characteristic of a full length SNX protein. Numerous examples of active fragments of an SNX are provided herein. Thus, a peptide having the amino acid sequence shown as amino acids 214 to 265 in SEQ ID NO: 2 encompasses the membrane trafficking domain of SNX1 and, therefore, is an example of an active fragment of an SNX. In addition, a peptide having the amino acid sequence shown as amino acids 465 to 522 in SEQ ID NO: 2 encompasses the EGFR binding domain of SNX1 and is another example of an active fragment of an SNX.

The peptide CKYLEAFLPEAKAIS (SEQ ID NO: 7) was used to raise an antibody that binds SNX1. This peptide corresponds to amino acids 509 to 522 of SNX1 (SEQ ID NO: 2), except that an amino terminal was added to facilitate coupling of the peptide to a resin (see Example II) and the leucine at position 4 in the peptide was substituted for the tryptophan at position 511 of SNX1 (SEQ ID NO: 2) so the peptide would be soluble. Thus, the amino acid sequence shown as amino acids 509 to 522 of SNX1 (SEQ ID NO: 2) provides another example of an active fragment of SNX1. In addition, amino acid sequences in SNX2 that correspond to the exemplified active fragments of SNX1 provide further examples of active fragments of an SNX. An active fragment of an SNX can be obtained using well known methods of recombinant DNA technology, for example, by expression of an appropriate nucleotide sequence of SEQ ID NO: 1 or SEQ ID NO: 3, or routine methods of chemical peptide synthesis and can be characterized using methods disclosed herein.

In view of the present disclosure, the skilled artisan would recognize that additional members of the SNX family of proteins can be involved in down regulating the cell surface expression of other cell surface receptors, including, for example, the PDGFR, the insulin receptor and the fibroblast growth factor receptor. Additional members of the SNX family of proteins that bind to and down regulate the expression of such receptors can be identified using methods disclosed herein. In addition, an SNX such as SNX1 or SNX2 can be modified so as to change the specificity of the SNX. For example, random or directed changes can be made to the EGFR binding site of SNX1 (residues 465–522) and the mutant SNX can be tested for its ability to bind a different member of the EGFR family of receptors or to bind to a different receptor such as a PDGFR or insulin receptor.

Methods for modifying a known amino acid sequence are routine and well known in the art. For example, a nucleic acid molecule such as that encoding SNX1 (SEQ ID NO: 1) can be synthesized, but containing one or a few nucleotide changes in the sequence encoding the EGFR binding domain. Upon expressing such a mutated SNX molecule, for example, in a construct useful in the two hybrid assay, the ability of the mutant SNX to bind one or more receptors such as the erbB-2 receptor or PDGFR can be examined (see Example I). A method such as that described by Ladner et al. (U.S. Pat. No. 5,223,409, issued Jun. 29, 1993, which is incorporated herein by reference) can be particularly useful for producing phage expressing varied SNX mutants. The phage library can be screened using one or more receptors or a receptor domain containing a putative lysosomal targeting code to identify phage expressing a mutant SNX that binds a particular receptor or a group of receptors. The method of Ladner can be particularly useful when combined with a method of codon based mutagenesis (U.S. Pat. No. 5,264,563, issued Nov. 23, 1993, which is incorporated herein by reference), which provides a means to produce a random population of diverse binding domains.

The present invention also provides antibodies that specifically bind with one or more members of the SNX family of proteins. Active fragments of antibodies such as Fv, Fab and Fab'$_2$ fragments that are specifically reactive with an SNX are included within the meaning of the term "antibody" as used herein. Thus, the term "antibody" includes, for example, chimeric antibodies, humanized antibodies, bifunctional and heterofunctional antibodies, which can contain antigen binding sites from two or more antibodies, and CDR-grafted antibodies. Antibodies exhibiting an affinity of at least about $1.5 \times 10^5$ $M^{-1}$ as determined, for example, by Scatchard analysis are useful in the present invention. An anti-SNX antibody can be characterized by its ability to bind a portion of an SNX protein.

An antibody of the invention can be produced and characterized as described herein or by any method known in the art. For example, an anti-SNX1 antibody was obtained by immunization of a rabbit with the peptide, CKYLEAFL-PEAKAIS (SEQ ID NO: 7), which corresponds to an active fragment of SNX1 present at the carboxy terminus of SNX1 (SEQ ID NO: 2; see Example II). Such an antibody is useful, for example, to detect the localization of SNX1 in a tissue sample (Example II). Since the peptide of SEQ ID NO: 7 corresponds to a portion of the EGFR binding domain of SNX1, an antibody raised using that peptide as an immunogen can be used to identify other proteins that contain an EGFR binding domain, including other members of the SNX family of proteins having this domain. In this regard, the anti-SNX1 antibody raised using the peptide of SEQ ID NO: 7 identified a 40 kDa endosome associated molecule in CV-1 monkey kidney cells, MCF7 breast cancer cells and A431 epidermoid carcinoma cells. It is recognized that the 40 kDa endosome associated molecule identified using the anti-SNX1 antibody can be SNX2, which has 93% sequence identity with SNX1 in the region corresponding to the peptide of SEQ ID NO: 7.

Polyclonal antibodies or monoclonal antibodies can be produced using the method disclosed herein or otherwise known in the art (see, for example, Harlow and Lane, *Antibodies: A Laboratory Manual* (Cold Spring Harbor Laboratory Press 1988), which is incorporated herein by reference). For example, an anti-SNX antibody can be obtained by immunizing rabbits with an active fragment of an SNX comprising the membrane trafficking domain such as the domain encompassed by amino acids 214 to 265 of SNX1 (SEQ ID NO: 2). Such an antibody can be useful for identifying the presence of an SNX in a sample or for identifying additional members of the SNX family of proteins containing this domain. An antibody of the invention also can be useful in various immunoassays such as an ELISA, a radioimmunoassay or a western blot assay (see Harlow and Lane, supra, 1988; chaps. 10–14).

Antibodies also can be produced, for example, by expression from a hybridoma cell line, by chemical synthesis or using recombinant methods (see Sambrook et al., *Molecular Cloning: A laboratory manual* (Cold Spring Harbor Laboratory Press 1989), which is incorporated herein by reference). Chimeric, humanized, CDR-grafted and bifunctional antibodies can be produced, for example, using methods well known to those skilled in the art (Harlow and Lane, 1988; see, also, Hilyard et al., *Protein Engineering: A practical approach* (IRL Press 1992); Borreabeck, *Antibody Engineering*, 2d ed. (Oxford University Press 1995); each of which is incorporated herein by reference).

An anti-SNX antibody can be useful to substantially purify SNX proteins from a sample containing such proteins. For example, an anti-SNX antibody can be attached to a solid support such as a gel chromatography matrix, added to a column and used to affinity purify an SNX from a sample added to the column. Methods for attaching an antibody to a solid support matrix and purifying an antigen by affinity chromatography are routine in the art (see Harlow and Lane, supra, 1988; chap. 13). Similarly, a nucleic acid molecule encoding an SNX can be obtained by screening, for example, a λgt11 cDNA library using an anti-SNX antibody, particularly an antibody specific for the membrane trafficking domain of an SNX, and isolating phage expressing a protein bound by the antibody.

An anti-SNX antibody can be detectably labelled using well known methods (see, for example, Harlow and Lane, 1988; chap. 9). For example, an antibody can be detectably labelled by attaching any of a variety of moieties, including biotin, an enzyme such as alkaline phosphatase, a fluorochrome or a radionuclide, such as technicium-99 or iodine-125. Following contact of a labelled antibody with a sample such as a tissue sample or a tissue homogenate or extract, specifically bound antibody can be identified by detecting the particular moiety. If desired, a labelled second antibody can be used to identify specific binding of an unlabeled first antibody such as an anti-SNX antibody. A second antibody is specific for the particular class of the first antibody. For example, if an anti-SNX antibody is a rabbit antibody of the IgG class, an anti-rabbit IgG antibody is an appropriate second antibody. Such second antibodies can be produced using well known methods or can be purchased from a commercial source. The second antibody also can be labelled as described above. When an SNX in a sample is detected using a second antibody, the sample is first contacted with a first antibody, then the sample is contacted with the labelled second antibody, which specifically binds to the first antibody, resulting in a detectably labelled complex.

The present invention also provides a substantially purified nucleic acid molecule encoding a member of the SNX family of proteins. A nucleic acid molecule of the invention is exemplified by SEQ ID NO: 1, which discloses a 1976 nucleotide sequence encoding full length SNX1 (SEQ ID NO: 2). In addition, a nucleic acid molecule of the invention is exemplified by SEQ ID NO: 3, which encodes SNX2 (SEQ ID NO: 4).

As used herein, the term "substantially purified," when used in reference to a nucleic acid molecule, means that the nucleic acid molecule is relatively free from contaminating materials such as lipids, proteins, carbohydrates or cellular material normally associated with a nucleic acid in a cell. For example, a nucleic acid molecule that is chemically synthesized or is produced using recombinant DNA methods is considered substantially purified. Recombinant DNA methods for producing a substantially purified nucleic acid molecule are well known in the art and include cloning the sequence or amplifying the sequence using the polymerase chain reaction (PCR; see Sambrook et al., 1989; see, also, Erlich, *PCR Technology: Principles and applications for DNA amplification* (Stockton Press 1989), which is incorporated herein by reference; see, also, Example I).

The invention provides a nucleic acid molecule encoding, for example, SNX1 (SEQ ID NO: 1) or SNX2 (SEQ ID NO: 3), as well as a nucleic acid molecule having substantially the nucleotide sequence of the nucleic acid molecule shown in SEQ ID NO: 1 or in SEQ ID NO: 3. As used herein, the term "substantially the nucleotide sequence" means a nucleotide sequence that contains different nucleotides than shown in SEQ ID NO: 1 or SEQ ID NO: 3, but that, as a result of the degeneracy of the genetic code, encodes the same amino acid sequence as shown in SEQ ID NO: 2 or SEQ ID NO: 4, respectively. Such degeneracy is well known in the art and readily determinable by inspecting a nucleotide sequence.

The invention also provides vectors comprising a nucleic acid molecule encoding an SNX and provides host cells containing the vector. Vectors are well known in the art and include, for example, cloning vectors and expression vectors, which can be plasmids or viral vectors (see, for example, Goedell, *Meth. Enzymol.*, Vol. 185 (Academic Press 1990), which is incorporated herein by reference). An expression vector comprising a nucleic acid molecule encoding an SNX can be particularly useful for expressing large amounts of an SNX protein, which can be purified and used, for example, as an immunogen to raise anti-SNX antibodies. A baculovirus vector is an example of a vector that can be used to express large amounts of an SNX such as SNX1 or SNX2. Expression vectors also can be useful for expressing an antisense nucleic acid, which is complementary to at least a portion of a nucleic acid molecule encoding an SNX, or for expressing a ribozyme, which can be specific for an SNX RNA. A vector comprising a nucleic acid molecule encoding an SNX or a portion thereof can further comprise a promoter or enhancer element, which can be constitutive or inducible and, if desired, can be tissue specific. Host cells, which can contain such vectors, are known in the art and are selected based on the particular vector.

The invention also provides nucleotide sequences, which can hybridize under relatively stringent conditions to at least a portion of a nucleic acid molecule encoding an SNX. Such a nucleotide sequence of the invention can be useful as a probe, for example, or can be used to express an active fragment of an SNX. Where a nucleotide sequence of the invention is to be used in a hybridization procedure, relatively stringent hybridization conditions can be determined empirically or can be estimated based, for example, on the relative GC:AT content of the hybridizing nucleotide sequence and the target sequence, the length of the hybridizing nucleotide sequence and the number, if any, of mismatches between the hybridizing nucleotide sequence and the target sequence (see, for example, Sambrook, supra, 1989). Depending on the intended use, a nucleotide sequence used in a hybridization procedure should be at least about ten nucleotides in length, for example, when used as a primer for PCR, or at least about 14 to 16 nucleotides in length, for example, when used as a probe in a hybridization assay such as a Southern blot, northern blot or other similar "blot" analysis (see, for example, Innis et al., *PCR Protocols: A guide to methods and applications* (Academic Press 1990), which is incorporated herein by reference; see, also, Sambrook et al., supra, 1989).

A nucleotide sequence useful in the invention can be prepared, for example, by restriction endonuclease digestion of a cloned nucleic acid molecule encoding an SNX, such as a nucleic acid molecule shown as SEQ ID NO: 1 or SEQ ID NO: 3, or by PCR amplification of all or a portion of such a nucleic acid molecule. A nucleotide sequence of the invention also can be chemically synthesized using well known methods or can be purchased from a commercial source.

A nucleotide sequence of the invention can be detectably labelled and used as a probe or can be used as a PCR primer, which can be labelled or unlabeled, as desired. Various moieties are useful as detectable labels, including, for example, radioactive, fluorescent, luminescent, magnetic or enzymatic labels. Methods for detectably labeling a nucleotide sequence are well known in the art (see, for example, Sambrook et al., 1989; see, also, Ausubel et al., *Current Protocols in Molecular Biology* (Greene 1995), which is incorporated herein by reference).

The present invention also provides a method of identifying an endosomal fraction of a cell by contacting the cell or a fraction of the cell with a probe such as an SNX polypeptide, an active fragment thereof, an anti-SNX antibody or a peptide having a lysosomal targeting code, under suitable conditions, which allow binding of the probe to an endosomal fraction, if present, such binding being detectable. Such a method is useful to identify compartments of the endosomal sorting pathway in vivo or to identify a sample containing endosomes in vitro.

Prior to the present invention, an endosomal or lysosomal fraction of a cell was identified using indirect methods. For example, a lysosomal fraction is identified by detecting the activity of a lysosomal enzyme such as β-hexosaminidase or β-galactosidase (see Deutscher, *Meth. Enzymol.*, Vol. 182, "Guide to Protein Purification" (Academic Press 1990), which is incorporated herein by reference). An endosomal fraction is identified by detecting the presence, for example, of the transferrin receptor, which is known to localize in endosomes following down regulation from the cell surface. Such methods, however, are indirect and cumbersome. For example, in order to identify the lysosomal fraction of a cell following density gradient centrifugation of a cell extract, each fraction obtained from the gradient must be assayed for the particular enzymatic activity. Furthermore, no method has been described for identifying a sorting endosome, which is the compartment in which the decision is made to recycle a receptor or to direct the receptor to a lysosome.

The present invention provides simple and direct methods of detecting an endosomal fraction, particularly a sorting endosome, of a cell, using a probe, which can specifically bind to an endosome or to an SNX present in the endosome. The term "probe," when used in reference to a method of detecting an endosomal fraction of a cell, means an SNX protein, an active fragment of an SNX protein comprising a membrane trafficking domain, an anti-SNX antibody, or a peptide comprising a lysosomal targeting code. As used herein, the term "endosomal fraction" means a membrane containing portion of the endocytic pathway, including, for example, an endosome such as a sorting endosome. An endosomal fraction can be contained in a living cell or can be present in an extract prepared from a cell (see Deutscher, supra, 1990).

In one embodiment of this invention, an SNX or an active fragment such as a peptide comprising the membrane trafficking domain of an SNX is expressed in a cell as a fusion protein with a reporter such as the green fluorescent protein. Such a fusion protein is useful as a probe in a method of the invention because it contains at least the portion of an SNX involved in sorting a cell surface receptor to a lysosome and because it is readily detectable. The movement of the labeled SNX in a living cell can be followed using photomicroscopy, thus allowing direct detection of the compartments of the endocytic pathway, including the sorting endosome compartment, which previously has not been identified. In addition, a cell extract can be prepared from the cells expressing the fusion protein, the extract can be fractionated, if desired, and the endosomal fraction can be identified by detecting the presence of the probe.

In another embodiment of this invention, an SNX or active fragment thereof is detectably labeled, then is contacted with a sample such as a histologic tissue sample or a fraction of a cell obtained, for example, by density gradient centrifugation of a cell extract. Again, detection of the labeled SNX probe identifies the endosomal fraction of the cell.

In still another embodiment of this invention, an anti-SNX antibody or a peptide comprising a lysosomal targeting code is used as a probe for detecting an endosomal fraction of a cell. Such a method relies on the ability of the antibody or the peptide to specifically bind to an SNX present in the endosomal fraction and provides a means to directly identify the localization of an SNX in a sorting endosome. For this method, the probe can be detectably labeled or, where the probe is an anti-SNX antibody, can be labeled indirectly using an appropriate second antibody.

A method for detecting an endosomal fraction of a cell must be performed under suitable conditions, which allow binding of the probe to the endosomal fraction, if present. Such suitable conditions can be determined empirically based, for example, on the conditions used in the methods disclosed in the Examples.

The present invention also provides a method of down regulating the expression of a cell surface receptor by expressing a nucleic acid molecule encoding an SNX in a cell expressing the receptor. Various cancers are characterized, in part, by the failure of a cell to down regulate a cell surface receptor following binding of the ligand or activation of the receptor. For example, malignant tumors such as breast cancer, ovarian cancer and glioblastoma can contain cancer cells with amplified and overexpressed EGFR or with mutant EGFR, which is constitutively active but is not down regulated (see, for example, Libermann et al., *Nature* 313:144–147 (1985); Klijn et al., *Endocrinol. Rev.* 13:3–17 (1992); Rajkumar and Gullick, *Breast Canc. Res. Treat.* 29:3–9 (1994); Moscatello et al., *Canc. Res.* 55:5536–5539 (1995)). As disclosed herein, an SNX can bind a cell surface receptor and down regulate expression of the receptor from the cell surface and, therefore, can be useful for down regulating the expression of a mutant cell surface receptor on a cancer cell. Thus, a nucleic acid molecule encoding an SNX protein can be useful as a medicament for treating a pathology such as a cancer that is characterized, at least in part, by the increased expression of a cell surface receptor or by the inability of a cell to down regulate the expression of a cell surface receptor.

A nucleic acid molecule encoding an SNX protein can be expressed in a cell using well known expression vectors and gene transfer methods (see, for example, Wu, *Meth. Enzymol.*, Vol. 217 (Academic Press 1993), which is incorporated herein by reference; see, also, Sambrook et al., supra, 1989). Numerous methods are available for introducing a nucleic acid molecule into a cell in vitro (Sambrook et al., supra, 1989). Vectors are particularly useful when the vector contains a promoter sequence, which can provide constitutive or inducible expression of a cloned nucleic acid sequence or, if desired, can provide tissue specific expression of the inserted nucleic acid molecule. Such vectors are well known in the art (see, for example, Goeddel, *Meth. Enzymol.*, Vol. 185. (Academic Press, Inc., 1990); Gacesa and Ramji, *Vectors: Essential data* (John Wiley and Sons 1994), each of which is incorporated herein by reference) and available from commercial sources.

A nucleic acid molecule encoding an SNX protein can be inserted into an expression vector such as a plasmid or a viral vector, which is introduced into a cell using well known methods such as transfection, transduction, electroporation or lipofection. Examples of useful viral vectors include adenovirus and adeno-associated vectors and herpes simplex virus (see, for example, Flotte, *J. Bioenerg. Biomemb.*, 25:37–42 (1993); Kirshenbaum et al., *J. Clin. Invest*, 92:381–387 (1993); Geller et al., *Proc. Natl. Acad. Sci.. USA* 87:8950–8954 (1990), each of which is incorporated herein by reference). A nucleic acid encoding an SNX also can be introduced into a cell using adenovirus-polylysine DNA complexes (Michael et al., *J. Biol. Chem.*, 268:6866–6869 (1993), which is incorporated herein by reference). In addition, a nucleic acid molecule can be introduced into a cell using methods which do not require the initial introduction of the nucleic acid molecule into a vector. For example, a nucleic acid molecule can be introduced into a cell using a cationic liposome preparation (Morishita et al., *J. Clin. Invest.*, 91:2580–2585 (1993), which is incorporated herein by reference).

Viral vectors that are compatible with a targeted cell are particularly useful for introducing a nucleic acid encoding an SNX into a cell. For example, recombinant adenoviruses having general or tissue-specific promoters can be used to deliver a nucleic acid encoding an SNX into a variety of cell types in various tissues and can direct expression of the nucleic acid in the target cell. Recombinant adeno-associated viruses also are useful for introducing a nucleic acid encoding an SNX into a cell. Such adenovirus based vectors are useful because the nucleic acid can stably integrate into the chromatin of quiescent non-proliferating cells (Lebkowski et al., *Mol. Cell. Biol.* 8:3988–3996 (1988), which is incorporated herein by reference).

Viral vectors can be particularly useful where it is desirable to introduce a nucleic acid encoding an SNX into a cell in a subject, for example, for gene therapy. Viruses are specialized infectious agents that can elude host defense mechanisms and can infect and propagate in specific cell types. In particular, the specificity of viral vectors for particular cell types can be utilized to target predetermined cell types. Thus, the selection of a viral vector will depend, in part, on the cell type to be targeted. For example, if a nucleic acid is to be introduced into a neuronal cell, then a viral vector such as a herpes simplex virus, which targets neuronal cells, can be used (Battleman et al., *J. Neurosci.* 13:941–951 (1993), which is incorporated herein by reference). Similarly, if a nucleic acid encoding an SNX is to be introduced into a cell of the hematopoietic system, then a vector based, for example, on a human immunodeficiency virus can be used (Carroll et al., *J. Cell. Biochem.* 17E:241 (1993), which is incorporated herein by reference). If desired, a viral vector or other vector can be constructed to express a nucleic acid encoding an SNX in a tissue specific manner by incorporating a tissue-specific promoter or enhancer into the vector (Dai et al., *Proc. Natl. Acad. Sci., USA* 89:10892–10895 (1992), which is incorporated herein by reference).

Retroviral vectors can be particularly useful for introducing a nucleic acid encoding an SNX into a cell (see, for example, Vogt and Verma, supra, 1995; Chap. 14). Retroviral vectors can be constructed either to function as infectious particles or to undergo only a single initial round of infection. In the former case, the genome of the virus is modified so that it maintains the necessary genes, regulatory sequences and packaging signals to synthesize new viral proteins and RNA. However, genes conferring oncogenic potential of the virus is destroyed. After the viral proteins are synthesized, the host cell packages the RNA into new viral particles, which can undergo further rounds of infection. The viral genome also is engineered to encode and express the desired recombinant gene.

When a retrovirus vector is used for gene transfer, replication competent retroviruses theoretically can develop by recombination between the retroviral vector and viral gene sequences in the packaging cell line utilized to produce the retroviral vector. However, packaging cell lines in which the production of replication competent virus by recombination has been reduced or eliminated can be used. In addition, all retroviral vector supernatants used to infect patient cells can be screened for replication competent virus by standard assays such as PCR and reverse transcriptase assays (see, for example, Rosenberg et al., *New Engl. J. Med.*, 323:570–578 (1990), which is incorporated herein by reference).

In the case of non-infectious viral vectors, the helper virus genome can be mutated to destroy the viral packaging signal required to encapsulate the RNA into viral particles. However, the helper virus retains structural genes required to package a co-introduced recombinant virus containing a gene of interest. Without a packaging signal, a viral particle will not contain a genome and, thus, cannot proceed through subsequent rounds of infection. Methods for constructing and using viral vectors are known in the art and reviewed, for example, in Miller and Rosman, *Biotechniques* 7:980–990 (1992), which is incorporated herein by reference. The specific type of vector will depend upon the intended application. These vectors are well known and readily available within the art or can be constructed by one skilled in the art.

For gene therapy, a vector containing a nucleic acid encoding an SNX can be administered to a subject by various methods. For example, if viral vectors are used, administration can take advantage of the target specificity of the virus. In such cases, there in no need to administer the vector locally at the diseased site. However, local administration can be a particularly effective method of administering a nucleic acid encoding an SNX. In addition, administration can be via intravenous or subcutaneous injection into the subject. Following injection, the viral vector circulates until it recognizes a host cell with the appropriate target specificity for infection. In addition, a vector can be administered into the cerebrospinal fluid, for example, if a cancer such as a glioblastoma is to be treated.

Receptor-mediated DNA delivery approaches also can be used to deliver a nucleic acid molecule encoding an SNX into cells in a tissue-specific manner using a tissue-specific ligand or an antibody that is non-covalently complexed with the nucleic acid molecule via a bridging molecule (Curiel et al., *Hum. Gene Ther.* 3:147–154 (1992); Wu and Wu, *J. Biol. Chem.* 262:4429–4432 (1987), each of which is incorporated herein by reference). Direct injection of a naked or a nucleic acid molecule encapsulated, for example, in cationic liposomes also can be used for stable gene transfer into non-dividing or dividing cells in vivo (Ulmer et al., *Science* 259:1745–1748 (1993), which is incorporated herein by reference). In addition, a nucleic acid molecule encoding an SNX can be transferred into cells in a tissue using the particle bombardment method (Williams et al., *Proc. Natl. Acad. Sci., USA* 88:2726–2730 (1991), which is incorporated herein by reference). Such nucleic acid molecules are linked to the appropriate nucleotide sequences as required for accurate transcription and translation.

A nucleic acid encoding an SNX can be administered by direct inoculation locally at the site of a cancer. Local administration can be advantageous because there is no dilution effect and, therefore, the likelihood that a majority of the targeted cells will be contacted with the nucleic acid molecule is increased. Thus, local inoculation can alleviate the targeting requirement necessary with other forms of administration and, if desired, a vector that infects all cell types in the inoculated area can be used. If expression is desired in only a specific subset of cells within an inoculated area, then a promotor, an enhancer or other expression element specific for the desired subset of cells can be linked to the nucleic acid molecule. It should be recognized, however, that it will not always be necessary to target specific cells because an SNX down regulates only activated cell surface receptors. Thus, expression of an SNX that is introduced into normal cells due, for example, to their proximity to the cancer cells being targeted is not expected to affect the normal cells, which either will not contain the particular cell surface receptor recognized by the SNX or, if they do express the particular cell surface receptor, will down regulate the receptor in a normal manner following ligand binding.

As disclosed herein, introduction of a nucleic acid molecule encoding an SNX into a cell and expression of the SNX results in a more rapid and greater amount of down regulation of a cell surface receptor (see Example III). These results indicate that the level of expression of a cell surface receptor can be decreased by expressing in the cell an SNX that can bind the receptor. Such a method can be particularly useful where expression of a cell surface receptor is not down regulated in a normal manner. The effectiveness of such a method can be examined using, for example, a mouse model for glioblastoma, which is characterized, in part, by aberrant down regulation of the erbB-1 encoded EGFR (Nishikawa et al., *Proc. Natl. Acad. Sci.. USA* 91:7727–7731 (1994), which is incorporated herein by reference). An expression vector containing a nucleic acid molecule encoding an SNX such as SNX1 is introduced into glioblastoma cells, which then are introduced into a mouse. The ability of SNX expression in the glioblastoma cells to down regulate EGFR expression is examined and the effect of down regulation of the EGFR on tumorigenicity of the glioblastoma cells is determined. Suppression of tumorigenicity of SNX transfected glioblastoma cells indicates that expression of an SNX in such a cancer cell can provide a therapeutic advantage to a cancer patient.

The following examples are intended to illustrate but not limit the present invention.

EXAMPLE I

IDENTIFICATION AND ISOLATION OF NUCLEIC ACIDS ENCODING SNX1 AND SNX2

This example describes methods for cloning the cDNA molecules encoding SNX1 and SNX2.

The yeast two hybrid assay (Zervos et al., *Cell* 72:223–232 (1993), which is incorporated herein by reference) was used to screen a HeLa cell derived cDNA to identify cDNA inserts encoding polypeptides that bind the human EGFR core tyrosine kinase domain. Using this method, a cDNA encoding the carboxy terminal 58 amino acids of SNX1 was isolated.

The two hybrid assay was performed in yeast strain EGY48 cells (MATa trp1 ura3 his3 LEU2::pLexAop6-LEU2) using the plasmids pEG202, pJG4–5, pSH18–34 or pRFHMI (Zervos et al., supra, 1993). The HeLa cell cDNA library was prepared using routine methods and inserted into pJG4–5 to produce pJG-cDNA (see, for example, Ausubel et al., *Current Protocols in Molecular Biology* (Greene, publ. 1995), which is incorporated herein by reference; see, also, Zervos et al., supra, 1993; Sambrook et al., supra, 1989). A cDNA encoding amino acid residues 663 to 958 of EGFR was obtained by PCR of the plasmid, pXER (Chen et al., *Nature* 328:820–823 (1987), which is incorporated herein by reference), using Pfu polymerase (Stratagene; La Jolla Calif.) and the primers, 5'-GATCCGTCGACGGGAGCTTGTGGAGCCTCTTACA-3' (SEQ ID NO: 8) and 5'-GGCTGCAGGTCGACTGAATGACAAGGTAGCGCTG-3' (SEQ ID NO: 9). The product was cloned into the Sal I site of the yeast LexA-fusion expression plasmid pEG202 to produce the EGFR core tyrosine kinase bait plasmid, pEG-EGFR (see FIG. 2A).

pJG-cDNA and pEG-EGFR were cotransformed into EGY48 cells and interactor clones were selected using leucine auxotrophy and galactose inducible β-gal activity. pJG-cDNA plasmids were recovered from positive yeast colonies using *E. coli* strain KC8 (pyrF::Tn5, hsdr, leuB600, trpC9830, lacD74, strA, galK, hisB436), then transformed into EGY48 yeast cells containing pRFHMI, which is a bait plasmid that expresses a LexA-bicoid fusion protein (Zervos et al., supra, 1993). pJG-cDNA clones expressing proteins that bound to the lexA-bicoid fusion protein were considered to express non-specific binding proteins and were eliminated from further analysis.

The 5'-termini of the HeLa cDNA inserts of positive pJG-cDNA plasmids were sequenced by cycle sequencing (Epicentre Technologies; Madison Wis.) using $^{35}$S-dATP and the primer (5'-GATGTTAACGATACCAGCCTCTTGCTGAGT-3'; SEQ ID NO: 10), which binds immediately upstream of the vector/cDNA fusion junction. The cDNA sequences were used to search the nucleotide sequence databases of the NCBI using the BLAST algorithm (Altschul et al., *J. Mol. Biol.* 215:403–410 (1990)).

A HeLa cell derived λgt11 cDNA library was purchased from Clontech (Palo Alto Calif.) and screened with a $^{32}$P-labeled oligonucleotide, 5'-CTTTCTCAAACCTCACTTCT-3'; SEQ ID NO: 11), which is complementary to the 5'-end of the SNX1 sequence isolated using the two hybrid assay. Six positive phage were plaque purified, the cDNA inserts were subcloned into the Eco RI site of pMOBII (Gold Biotechnology; St. Louis Mo.), and transposon insertions were used to determine the complete sequence of two inserts on both strands (Strathmann et al., *Proc. Natl. Acad. Sci., USA* 88:1247–1250 (1991), which is incorporated herein by reference). A 1974 base pair SNX1 cDNA (SEQ ID NO: 1) encoding the full length SNX1 protein was obtained. Northern blot analysis revealed the presence of an abundant 2 kb SNX1 mRNA and a less abundant 8 kb mRNA that were widely expressed in various human tissues.

A database search using the cloned SNX1 cDNA sequence also identified a human expressed sequence tag (EST; GenBank Accession No. T63907), which encoded an amino acid sequence that is 70% identical to amino acids 465 to 522 of SNX1 (SEQ ID NO: 2), including part of the carboxy terminal EGFR binding domain. A plasmid containing the EST (clone 80063) was obtained from the I.M.A.G.E. Consortium (Lawrence Livermore National Laboratory). Upon sequencing clone 80063 obtained from the I.M.A.G.E. Consortium, 31 errors were found as compared to the sequence in GenBank Accession No. T63907, including 16 incorrect bases and 15 bases that were listed in GenBank but were not present in the sequenced clone 80063.

Based on the EST sequence, the primers 5'-TTGCTTCAGCTTCACGTTTTTTGAGCAA-3' (SEQ ID NO: 12) and 5'-TGACCATCGAATGAAGTGCTGGCAGAA-3' (SEQ ID NO: 13) were synthesized and used to clone the entire cDNA sequence (SEQ ID NO: 3) using the RACE method (Dumas et al., *Nucl. Acids Res.* 19:5227–5232 (1991), which is incorporated herein by reference). The cDNA contained 1599 nucleotides. The longest open reading frame encoded a 452 amino acid protein (see FIG. 1; SEQ ID NO: 4), which was designated SNX2 based on its homology to SNX1. The sequence of the EST corresponded to nucleotides 1225 to 1599 of the nucleic acid molecule encoding SNX2 (SEQ ID NO: 3) and encodes amino acids 335 to 451 of SNX2 (SEQ ID NO: 4). This region of SNX2 shares 69.5% sequence identity and 84.7% sequence homology with SNX1. These results indicate that the sorting nexins comprise a family of proteins sharing a related sequence homology.

EXAMPLE II

CHARACTERIZATION OF THE SNX1 AND SNX2 PROTEINS

This example provides a characterization of the SNX1 and SNX2 proteins.

The full length SNX1 cDNA (SEQ ID NO: 1) encodes a 522 amino acid hydrophilic protein (SEQ ID NO: 2; see FIG. 1) having a calculated molecular mass of 59.2 kDa. A database search using the SNX1 amino acid sequence identified an 83 amino acid sequence of SNX1 (residues 182–265; underlined in FIG. 1) that has 31% identity with a portion of the yeast Mvp1 protein, which is involved in pCPY receptor trafficking in yeast (Ekena and Stevens, supra, 1995). These results indicate that a domain encompassed within amino acids 182 to 265 of SNX1 comprises its membrane trafficking domain.

The SNX1 cDNA (SEQ ID NO: 1) was used to program a coupled in vitro transcription/translation reaction (Promega Corporation; Madison Wis.) containing $^{35}$S-methionine. The translation products were separated by gel electrophoresis and visualized by fluorography. The predominant product was a 66 kDa $^{35}$S-labeled protein, which is similar to the 59.2 kDa molecular mass calculated from the amino acid sequence (SEQ ID NO: 2).

A native 66 kDa SNX1 protein also was detected by western blot analysis of detergent extracts (1% Triton X-100, 50 mM HEPES, pH 7.4, 10% glycerol, 75 mM NaCl) prepared from various cell lines, including 293, HeLa, CV-1 and 3T3 cells. For western blot analysis, proteins in the detergent extracts were separated by SDS-PAGE, then transferred to nitrocellulose filters using standard methods (see, for example, Harlow and Lane, supra, 1988).

An affinity purified anti-SNX1 antibody was prepared by immunizing rabbits with the peptide CKYLEAFLPEAKAIS (SEQ ID NO: 7) conjugated to bovine serum albumin (BSA). Following immunization, rabbit serum was collected and the anti-SNX1 antibody was purified by affinity chromatography using the immunizing peptide conjugated to ovalbumin and immobilized on agarose beads. Anti-BSA antibodies were depleted by chromatography on BSA agarose. Specificity of the anti-SNX1 antibody was confirmed by preadsorbing the antibody solution with 1 mM immunizing peptide. Western blot analysis was performed using routine methods (Harlow and Lane, supra, 1988). The identification of a 66 kDa SNX1 protein in the various cell lines demonstrates that the cloned SNX1 cDNA sequence encodes the full length SNX1 protein.

The distribution of SNX1 in CV-1 cells engineered to overexpress SNX1 (see Example III.B.) was examined by indirect immunofluorescence. Cells were fixed in paraformaldehyde, permeabilized with saponin, and stained with the anti-SNX1 antibody, then Texas Red-conjugated goat anti-rabbit IgG (Molecular Probes, Inc.; Eugene OR) was added and SNX1 was visualized using epifluorescence illumination. SNX1 staining was localized to a perinuclear vesicular compartment. SNX1 distribution also was examined by isopycnic density gradient centrifugation and was found to cofractionate with endosomes containing EGFR and also with the cytosol fraction.

Western blot analysis of detergent extracts of CV1 cells, MCF7 cells and A431 cells using the anti-SNX1 antibody also revealed the presence of a band having an apparent molecular mass of about 40 kDa. This molecular mass is substantially less than the 51.68 kDa calculated molecular weight for SNX2. This discrepancy can be due to aberrant migration of SNX2 by SDS-PAGE; can indicate that the first methionine in the open reading frame deduced from the SNX2 cDNA sequence (SEQ ID NO: 3) is not the initiator methionine; can indicate that SNX2 is post-translationally modified by deletion of a portion of the N-terminus; or can indicate that the 40 kDa protein is a member of the SNX family of proteins other than SNX1 and SNX2.

Inspection of the amino acid sequence of SNX2 (SEQ ID NO: 4) as deduced from the SNX2 cDNA (SEQ ID NO: 3) revealed that the methionine residue present as amino acid 93 has a translation initiation site that conforms to the Kozak consensus sequence (Kozak, *J. Biol. Chem.* 266:19867–19870 (1991)) and, therefore, may be the first residue in SNX2. SNX1 does not contain a methionine residue in the position corresponding to amino acid 93 in SNX2 (see FIG. 1). Furthermore, the calculated molecular weight for SNX2 containing amino acids 93 to 452 as shown in FIG. 1 (SEQ ID NO: 4) is about 41.48 kDa, which is similar to the apparent molecular mass determined by SDS-PAGE. These results indicate that the methionine at position 93 can be the initiator methionine for SNX2 and that SNX2 has the sequence shown as amino acids 93 to 452 in SEQ ID NO: 4. Antibodies raised against peptides corresponding, for example, to amino acids 1 to 20 and to amino acids 93 to 113 of SNX2 as shown in FIG. 1 (SEQ ID NO: 2) can be useful for determining whether the 40 kDa protein is SNX2 and, if so, the reason for the discrepancy in the molecular weight of SNX2 as calculated from the deduced amino acid sequence of SEQ ID NO: 2 and the apparent molecular mass as determined by SDS-PAGE.

EXAMPLE III

SNX1 BINDS THE EGFR AND DIRECTS TRANSLOCATION OF THE EGFR TO LYSOSOMES

This example demonstrates that SNX1 binds to the EGFR and directs translocation of the EGFR to lysosomes in a cell, thereby down regulating cell surface expression of the receptor.

A. SNX1 binds the EGFR:

The yeast two hybrid assay was used to identify structural features of the EGFR necessary for binding SNX1. Various portions of the EGFR or of erbB-2 (see FIG. 2A) were fused to the DNA binding domain of LexA and examined for the ability to interact with the carboxy terminal 58 amino acids of SNX1 fused to the B42 acid patch transcriptional activation domain (Zervos et al., supra, 1993).

Expression of the SNX1-B42 transactivation domain fusion protein was under control of the GAL4 promoter. Expression from the plasmid encoding this fusion protein occurs when yeast cell containing the plasmid are grown in galactose containing medium. A specificity control for "spontaneous" activating mutations is performed by substituting dextrose for galactose in the medium (see FIG. 2A; see, also, below).

cDNA sequences encoding EGFR residues 647–1186, 647–957 or 647–942 (see FIG. 2A) were generated by PCR with Pfu polymerase using a human EGFR cDNA and the products were cloned into the yeast LexA-fusion expression plasmid pEG202. The rat erbB-2 core tyrosine kinase domain was generated by PCR and corresponds to EGFR amino acid positions 647–973 (Bargmann et al., supra, 1986).

PCR primers used to produce the constructs shown in FIG. 2A were as follows:

(1) EGFR amino acids 663 to 958, 5'-GATCCGTC GACGGGAGCTTGTGGAGCCTCTTACA-3' (SEQ ID NO: 14) and 5'-GGCTGCAGGTCGAC TGAATGACAAGGTAGCGCTG-3' (SEQ ID NO: 15);

(2) EGFR amino acids 647 to 1186, 5'-GATCCC ATGGCGCCACATCGTTCGGAAGCG-3' (SEQ ID NO: 16) and 5'-CCCCTCGAGGTCGACGGTATC GATAAGCTT-3' (SEQ ID NO: 17);

(3) EGFR amino acids 647 TO 957, 5'-GATCCCAT GGCGCCACATCGTTCGGAAGCG-3' (SEQ ID NO: 16) and 5'-CCCCTCGAGGTCGA CGGTATCGATAAGCTT-3' (SEQ ID NO: 17);

(4) EGFR amino acids 647 to 942, 5'-GATCCC ATGGCGCCACATCGTTCGGAAGCG-3' (SEQ ID NO: 16) and 5'-GATCCTCGAGGATGATCA ACTCACGGAACTT-3' (SEQ ID NO: 18);

(5) erbB-2 KD, 5'-GATCCGTCGACGGCAGAAG ATCCGGAAGTAT-3' (SEQ ID NO: 19) and 5'-GGC TGCAGGTCGACGGTACTGTCCATGGGGCTGG A-3' (SEQ ID NO: 20).

Appropriate combinations of EGFR or erbB-2 constructs and SNX1 constructs were cotransformed into yeast EGY48 cells. Log phase yeast cultures were diluted into ura⁻his⁻trp⁻ broth containing 2% dextrose (control) or 2% galactose (to induce the library plasmid insert) and grown at 30° C. for 18–22 hr. Extracts were prepared from cells and assayed for β-gal activity (FIG. 2A).

Coexpression of a construct containing the EGFR core tyrosine kinase domain (residues 663–958) and the SNX1 construct resulted in a 400x induction of β-gal activity in response to galactose induction (FIG. 2A. This result demonstrates that the EGFR core tyrosine kinase domain can bind the SNX1 carboxy terminal domain. Expression of the EGFR core tyrosine kinase domain (amino acids 647–957) produced an even greater amount of β-gal activity. However, truncation of the tyrosine kinase domain to amino acids 647–942 substantially diminished its ability to interact with SNX1.

These results indicate that a 14 amino acid domain comprising amino acid residues 945 to 958 of the core tyrosine kinase domain is required for SNX1 to bind the EGFR with high affinity. This 14 amino acid domain of EGFR contains a consensus tetrapeptide lysosomal targeting code, YLVI (SEQ ID NO: 5; see FIG. 2B; see, also, Opresko et al., *J. Biol. Chem.* 270:6320–6327 (1990)). The proteins encoded by human erbB-3 and erbB-4 also contain the YLVI (SEQ ID NO: 5) tetrapeptide lysosomal targeting code, indicating that SNX1 or another member of the SNX family of proteins can be involved in sorting these receptors to a lysosome.

In contrast, a construct containing the entire intracellular domain of the EGFR (residues 647–1186) failed to interact with SNX1. This result is consistent with studies in which anti-phosphotyrosine antibodies failed to recognize the 647–1186 EGFR intracellular domain in yeast and indicates that an autophosphorylation-dependent conformational change is required to expose a cryptic binding site in the holo EGFR (see Cadena et al., *J. Biol. Chem.* 269:260–265 (1994); Nesterov et al., *J. Biol. Chem.* 270:6320–6327 (1995), each of which is incorporated herein by reference).

SNX1 also failed to bind the region of the rat erbB-2 receptor that corresponds to the EGFR core tyrosine kinase domain (see FIG. 2). Notably, the sequence in erbB-2 (and in neu) that corresponds to the EGFR tetrapeptide lysosomal targeting code does not contain a consensus lysosomal targeting code (FIG. 2B; see, also, Letourneur and Klausner, supra, 1992; Johnson and Kornfeld, supra, 1992). This result indicates that a lysosomal targeting code is required for SNX1 binding to the EGFR.

To confirm that the carboxy terminal domain of SNX1 contains the EGFR binding domain, an SNX1 truncation mutant lacking amino acid residues 456–522 was constructed. Deletion of this carboxy terminal domain from SNX1 abolished the inhibitory activity of SNX1 on expression of cotransfected EGFR in 293 cells. Similarly, EGFR was not down regulated in CV-1 cells transfected with this carboxy terminal truncated SNX1 mutant. These results demonstrate that SNX1 binds to the EGFR and that the carboxy domain of SNX1 and a domain including the lysosomal targeting code in EGFR are required for this interaction.

B. SNX1 binding directs EGFR translocation to a lysosome:

The ability of SNX1 to target the human EGFR to a lysosome was demonstrated in clones of CV-1 cells that were stably transfected and express high levels of SNX1. CV-1 cell were transfected with the vector pCEP4 (Invitrogen; San Diego Calif.) containing the SNX1 cDNA (SEQ ID NO: 1). Cells were plated on 6 cm plates and transfected with calcium phosphate DNA coprecipitates (15 $\mu$g/2×10$^6$ cells) for 4 to 6 hr (Graham and van der Eb, *Virology* 52:456–467 (1973), which is incorporated herein by reference). Transfected CV-1 cells were expanded for 48 hr after transfection, then transferred to 10 cm plates. Stable transfectants were selected by growing the cells in the presence of 320 $\mu$g/ml hygromycin for 14 to 21 days and clonal SNX transfected cell lines were isolated.

EGFR expression in the stably transfected CV-1 cells was analyzed by indirect immunofluorescence. CV-1 transfectants were fixed in paraformaldehyde and permeabilized with saponin, then stained with a mixture of anti-EGFR antibodies (IgG 528, IgG 13A9, IgG 225; Kawamoto et al., *Proc. Natl. Acad. Sci., USA* 80:1337–1341 (1983), which is incorporated herein by reference) followed by FITC conjugated goat anti-mouse IgG, and visualized using epifluorescence illumination. In some experiments, the cells were treated with 10 nM EGF for 30 min to determine the rate of EGFR down regulation in the presence of ligand.

Strong surface EGFR staining was observed on control CV-1 cells transfected with vector alone. In contrast, surface EGFR staining was greatly reduced on SNX1 transfected CV-1 cells. Instead, EGFR was localized in the same perinuclear vesicular compartment that accumulated EGFR following exposure of vector control transfected CV-1 cells to EGF.

Fifteen SNX1 transfected clonal CV-1 cell lines also were analyzed quantitatively by flow cytometry for surface EGFR expression. Eight of the cell lines were highly deficient in surface EGFR relative to vector control transfected cells. Scatchard analysis of $^{125}$I-EGF binding revealed a 75% reduction in the number of receptors at the cell surface (SNX1 transfectants, Kd=1.34 nM, 12,100 receptors/cell; vector transfected control cells, Kd=0.73 nM, 52,200 receptors/cell).

In all EGFR deficient lines analyzed, down regulation of surface EGFR by SNX1 was paralleled by a decrease in the steady-state EGFR mass in cell lysates; the steady-state EGFR mass was further diminished by treatment with 10 nM EGF for 30 minutes. Whole cell lysates (1% SDS, 10 mM HEPES, pH 7.4; buffers were supplemented with protease and phosphatase inhibitors as follows: 10 mM NaF, 1 mM Na vanadate, 1 mM EDTA, 1 mM EGTA, 1 mM PMSF, 10 mM benzamidine, 10 $\mu$g/ml leupeptin 10 $\mu$g/ml antipain, 10 $\mu$g/ml aprotinin) were prepared from serum starved CV-1 cells incubated in the absence or presence of 10 nM EGF for 3 min. Lysates were examined by western blot analysis using antibodies specific for EGFR (rabbit polyclonal 1964), erbB-2 (rabbit polyclonal 1917), PDGFR (Transduction Lab.; Lexington Ky.) or SNX1 (see Example I).

In cloned SNX1 transfected CV-1 cell lines that retained higher concentrations of EGFR, addition of EGF caused a much more rapid degradation of EGFR compared to the rate of degradation in vector control transfected cells. Overexpression of SNX1 in the transfected CV-1 cells did not alter erbB-2 or PDGFR levels, thus demonstrating that down regulation of EGFR by SNX1 is specific.

EGFR half life was determined in the stably transfected CV-1 cell. CV-1 cell were grown for 2 hr in DME lacking methionine and containing 10% dialyzed calf serum, then pulsed with 0.65 mCi/ml $^{35}$S-methionine for 1 hr. Cells then were incubated in complete medium and RIP (1% sodium deoxycholate, 1% NP-40, 0.1% SDS, 10 mM HEPES, pH 7.6, 150 mM NaCl, supplemented with protease and phosphatase inhibitors, as above) extracts were prepared after various periods of time. Extracts were immunoprecipitated using anti-EGFR antibodies 528 and 13A9 and the immunoprecipates were washed, solubilized in SDS sample buffer, separated by electrophoresis and visualized by fluorography; radioactivity also was quantitated by liquid scintillation counting.

Over-expression of SNX1 decreased the half life of EGFR from 12 hr to 2 hr. Furthermore, at the end of the 1 hr pulse, similar amounts of full-length $^{35}$S-labeled EGFR were observed in vector and SNX1 transfected CV-1 cells, indicating that the reduction in steady-state EGFR mass did not reflect a change in synthesis or Golgi processing but was due entirely to accelerated turnover. The half-life in SNX1 transfected cells that retained higher cell surface EGFR concentrations was more similar to vector transfected cells.

Since selective pressure to maintain a critical level of EGFR signaling could account for clonal variation in EGFR expression in the SNX1 stably transfected CV-1 cells, a transient transfection assay was used to confirm that SNX1 can down regulate cotransfected EGFR under nonselective conditions. CMV enhancer/promoter driven SNX1 and EGFR cDNA sequences were cotransfected into 293 cells. The EGFR expression plasmid was constructed by cleaving pRc/CMV (Stratagene) with Hind III, then filling-in the overhangs with the Klenow fragment of DNA polymerase. The Xba I/Apa I polylinker portion of the pBluescript™ plasmid (Stratagene) was inserted into the Xba I/Apa I site at the 3'-end of the pRc/CMV polylinker and the EGFR from PXER (Chen et al., supra, 1987) was cloned into the Xba I/Hind III of the modified pRc/CMV plasmid. After 48 hr, the cells were treated with various concentrations of EGF for 30 min, then lysates were prepared and analyzed by western blot analysis using anti-EGFR (1964) and anti-phosphotyrosine (PY20) antibodies (Transduction Lab.), which recognize autophosphorylated EGFR.

In agreement with the down regulation of endogenous EGFR observed in the SNX1 transfected CV-1 cells, fewer EGFR were expressed on the surface of SNX1 transfected 293 cells than on the surface of vector control transfected 293 cells. EGF induced activation of the EGFR remaining on the cell surface of the transfected 293 cells. These results demonstrate that SNX1 binding to the EGFR down regulates expression of the receptor from the surface of a cell.

Although the invention has been described with reference to the examples above, it should be understood that various modifications can be made without departing from the spirit of the invention. Accordingly, the invention is limited only by the following claims.

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 1974 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 46..1612

( x i ) SEQUENCE DESCRIPTION: SEQ ID NO:1:

```
CGGGATCAAT  TTGATTTGAC  AGTCGGTATA  ACTGATCCTG  AGAAG ATG GCG TCG                54
                                                      Met Ala Ser
                                                       1

GGT GGT GGT GGC TGT AGC GCT TCG GAG AGA CTG CCT CCG CCC TTC CCC                 102
Gly Gly Gly Gly Cys Ser Ala Ser Glu Arg Leu Pro Pro Pro Phe Pro
     5               10                  15

GGC CTG GAG CCG GAG TCC GAG GGG GCG GCC GGG GGA TCA GAA CCC GAG                 150
Gly Leu Glu Pro Glu Ser Glu Gly Ala Ala Gly Gly Ser Glu Pro Glu
 20              25                  30                  35

GCT GGG GAC AGC GAC ACC GAG GGG GAG GAC ATT TTC ACC GGC GCC GCG                 198
Ala Gly Asp Ser Asp Thr Glu Gly Glu Asp Ile Phe Thr Gly Ala Ala
                 40                  45                  50

GTG GTC AGT AAA CAT CAG TCT CCA AAG ATA ACT ACA TCC CTT CTT CCC                 246
Val Val Ser Lys His Gln Ser Pro Lys Ile Thr Thr Ser Leu Leu Pro
             55                  60                  65

ATC AAC AAT GGC TCC AAA GAA AAT GGG ATC CAT GAA GAA CAA GAC CAA                 294
Ile Asn Asn Gly Ser Lys Glu Asn Gly Ile His Glu Glu Gln Asp Gln
         70                  75                  80

GAG CCA CAG GAT CTC TTT GCA GAT GCC ACA GTG GAG CTA TCC TTG GAC                 342
Glu Pro Gln Asp Leu Phe Ala Asp Ala Thr Val Glu Leu Ser Leu Asp
     85                  90                  95

AGC ACA CAA AAT AAT CAG AAG AAG GTG CTA GCC AAA ACA CTC ATT TYT                 390
Ser Thr Gln Asn Asn Gln Lys Lys Val Leu Ala Lys Thr Leu Ile Xaa
100                 105                 110                 115

CTT CCT CCT CAG GAA GCC ACA AAT TCT TCG AAG CCC CAG CCA ACC TAT                 438
Leu Pro Pro Gln Glu Ala Thr Asn Ser Ser Lys Pro Gln Pro Thr Tyr
                    120                 125                 130

GAG GAG CTA GAG GAA GAA GAA CAG GAG GAT CAA TTT GAT TTG ACA GTC                 486
Glu Glu Leu Glu Glu Glu Glu Gln Glu Asp Gln Phe Asp Leu Thr Val
             135                 140                 145
```

| | | | | | | | | | | | | | | | | |
|---|---|---|---|---|---|---|---|---|---|---|---|---|---|---|---|---|
| GGT | ATA | ACT | GAT | CCT | GAG | AAG | ATA | GGG | GAT | GGT | ATG | AAT | GCA | TAT | GTA | 534 |
| Gly | Ile | Thr | Asp | Pro | Glu | Lys | Ile | Gly | Asp | Gly | Met | Asn | Ala | Tyr | Val | |
| | 150 | | | | | 155 | | | | | 160 | | | | | |
| GCC | TAC | AAA | GTT | ACA | ACA | CAG | ACA | AGC | TTA | CCA | TTG | TTC | AGA | AGC | AAA | 582 |
| Ala | Tyr | Lys | Val | Thr | Thr | Gln | Thr | Ser | Leu | Pro | Leu | Phe | Arg | Ser | Lys | |
| | 165 | | | | | 170 | | | | | 175 | | | | | |
| CAG | TTT | GCA | GTA | AAA | AGA | AGA | TTT | AGT | GAC | TTT | CTG | GGT | CTT | TAT | GAG | 630 |
| Gln | Phe | Ala | Val | Lys | Arg | Arg | Phe | Ser | Asp | Phe | Leu | Gly | Leu | Tyr | Glu | |
| 180 | | | | | 185 | | | | | 190 | | | | | 195 | |
| AAG | CTT | TCC | GAG | AAG | CAC | TCT | CAG | AAT | GGC | TTC | ATT | GTC | CCT | CCG | CCC | 678 |
| Lys | Leu | Ser | Glu | Lys | His | Ser | Gln | Asn | Gly | Phe | Ile | Val | Pro | Pro | Pro | |
| | | | | 200 | | | | | 205 | | | | | 210 | | |
| CCG | GAG | AAG | AGC | CTC | ATA | GGG | ATG | ACA | AAA | GTG | AAA | GTT | GGG | AAG | GAA | 726 |
| Pro | Glu | Lys | Ser | Leu | Ile | Gly | Met | Thr | Lys | Val | Lys | Val | Gly | Lys | Glu | |
| | | | 215 | | | | | 220 | | | | | 225 | | | |
| GAT | TCT | TCT | TCT | GCA | GAA | TTT | CTT | GAA | AAA | CGG | AGG | GCC | GCT | TTA | GAA | 774 |
| Asp | Ser | Ser | Ser | Ala | Glu | Phe | Leu | Glu | Lys | Arg | Arg | Ala | Ala | Leu | Glu | |
| | | 230 | | | | | 235 | | | | | 240 | | | | |
| AGG | TAC | CTT | CAG | AGG | ATT | GTA | AAT | CAT | CCT | ACC | ATG | TTA | CAG | GAC | CCT | 822 |
| Arg | Tyr | Leu | Gln | Arg | Ile | Val | Asn | His | Pro | Thr | Met | Leu | Gln | Asp | Pro | |
| | 245 | | | | | 250 | | | | | 255 | | | | | |
| GAC | GTC | AGA | GAG | TTC | TTG | GAA | AAA | GAA | GAG | CTG | CCA | CGT | GCC | GTG | GGT | 870 |
| Asp | Val | Arg | Glu | Phe | Leu | Glu | Lys | Glu | Glu | Leu | Pro | Arg | Ala | Val | Gly | |
| 260 | | | | | 265 | | | | | 270 | | | | | 275 | |
| ACC | CAG | ACA | TTG | AGT | GGT | GCT | GGT | CTC | CTC | AAG | ATG | TTC | AAC | AAA | GCC | 918 |
| Thr | Gln | Thr | Leu | Ser | Gly | Ala | Gly | Leu | Leu | Lys | Met | Phe | Asn | Lys | Ala | |
| | | | | 280 | | | | | 285 | | | | | 290 | | |
| ACA | GAT | GCC | GTC | AGC | AAA | ATG | ACC | ATC | AAG | ATG | AAT | GAA | TCA | GAC | ATT | 966 |
| Thr | Asp | Ala | Val | Ser | Lys | Met | Thr | Ile | Lys | Met | Asn | Glu | Ser | Asp | Ile | |
| | | | 295 | | | | | 300 | | | | | 305 | | | |
| TGG | TTT | GAG | GAG | AAG | CTC | CAG | GAG | GTA | GAG | TGT | GAG | GAG | CAG | CGC | TTA | 1014 |
| Trp | Phe | Glu | Glu | Lys | Leu | Gln | Glu | Val | Glu | Cys | Glu | Glu | Gln | Arg | Leu | |
| | | 310 | | | | | 315 | | | | | 320 | | | | |
| CGG | AAA | CTG | CAT | GCT | GTT | GTA | GAA | ACT | CTA | GTC | AAC | CAT | AGG | AAA | GAG | 1062 |
| Arg | Lys | Leu | His | Ala | Val | Val | Glu | Thr | Leu | Val | Asn | His | Arg | Lys | Glu | |
| | 325 | | | | | 330 | | | | | 335 | | | | | |
| CTA | GCG | CTG | AAC | ACA | GCC | CAG | TTT | GCA | AAG | AGT | CTA | GCC | ATG | CTT | GGG | 1110 |
| Leu | Ala | Leu | Asn | Thr | Ala | Gln | Phe | Ala | Lys | Ser | Leu | Ala | Met | Leu | Gly | |
| 340 | | | | | 345 | | | | | 350 | | | | | 355 | |
| AGC | TCT | GAG | GAC | AAC | ACG | GCA | TTG | TCA | CGG | GCA | CTC | TCC | CAG | CTG | GCT | 1158 |
| Ser | Ser | Glu | Asp | Asn | Thr | Ala | Leu | Ser | Arg | Ala | Leu | Ser | Gln | Leu | Ala | |
| | | | | 360 | | | | | 365 | | | | | 370 | | |
| GAG | GTG | GAA | GAA | AAA | ATT | GAG | CAG | CTC | CAC | GAA | CAG | GCC | AAC | AAT | | 1206 |
| Glu | Val | Glu | Glu | Lys | Ile | Glu | Gln | Leu | His | Gln | Glu | Gln | Ala | Asn | Asn | |
| | | | 375 | | | | | 380 | | | | | 385 | | | |
| GAC | TTC | TTC | CTC | CTT | GCT | GAG | CTC | CTG | AGT | GAC | TAC | ATT | CGC | CTC | CTG | 1254 |
| Asp | Phe | Phe | Leu | Leu | Ala | Glu | Leu | Leu | Ser | Asp | Tyr | Ile | Arg | Leu | Leu | |
| | 390 | | | | | 395 | | | | | 400 | | | | | |
| GCC | ATA | GTC | CGC | GCT | GCC | TTC | GAC | CAG | CGC | ATG | AAG | ACA | TGG | CAG | CGC | 1302 |
| Ala | Ile | Val | Arg | Ala | Ala | Phe | Asp | Gln | Arg | Met | Lys | Thr | Trp | Gln | Arg | |
| 405 | | | | | 410 | | | | | 415 | | | | | | |
| TGG | CAG | GAT | GCC | CAA | GCC | ACA | CTG | CAG | AAG | AAG | CGG | GAG | GCC | GAG | GCT | 1350 |
| Trp | Gln | Asp | Ala | Gln | Ala | Thr | Leu | Gln | Lys | Lys | Arg | Glu | Ala | Glu | Ala | |
| 420 | | | | | 425 | | | | | 430 | | | | | 435 | |
| CGG | CTG | CTG | TGG | GCC | AAC | AAG | CCT | GAT | AAG | CTG | CAG | CAG | GCC | AAG | GAC | 1398 |
| Arg | Leu | Leu | Trp | Ala | Asn | Lys | Pro | Asp | Lys | Leu | Gln | Gln | Ala | Lys | Asp | |
| | | | | 440 | | | | | 445 | | | | | 450 | | |
| GAG | ATC | CTC | GAG | TGG | GAG | TCT | CGG | GTG | ACT | CAA | TAT | GAA | AGG | GAC | TTC | 1446 |
| Glu | Ile | Leu | Glu | Trp | Glu | Ser | Arg | Val | Thr | Gln | Tyr | Glu | Arg | Asp | Phe | |
| | | | 455 | | | | | 460 | | | | | 465 | | | |

| | | | | | | | | | | | | | | | | |
|---|---|---|---|---|---|---|---|---|---|---|---|---|---|---|---|---|
| GAG | AGG | ATT | TCA | ACA | GTG | GTC | CGA | AAA | GAA | GTG | ATA | CGG | TTT | GAG | AAA | 1494 |
| Glu | Arg | Ile | Ser | Thr | Val | Val | Arg | Lys | Glu | Val | Ile | Arg | Phe | Glu | Lys | |
| | | 470 | | | | | 475 | | | | | 480 | | | | |
| GAG | AAA | TCC | AAG | GAC | TTC | AAG | AAC | CAC | GTG | ATC | AAG | TAC | CTT | GAG | ACA | 1542 |
| Glu | Lys | Ser | Lys | Asp | Phe | Lys | Asn | His | Val | Ile | Lys | Tyr | Leu | Glu | Thr | |
| | 485 | | | | | 490 | | | | | 495 | | | | | |
| CTC | CTT | TAC | TCA | CAG | CAG | CAG | CTG | GCA | AAG | TAC | TGG | GAA | GCC | TTC | CTT | 1590 |
| Leu | Leu | Tyr | Ser | Gln | Gln | Gln | Leu | Ala | Lys | Tyr | Trp | Glu | Ala | Phe | Leu | |
| 500 | | | | | 505 | | | | | 510 | | | | | 515 | |
| CCT | GAG | GCA | AAG | GCC | ATC | TCC | T AATGGACCAA | | GGACCCCAGA | | GCCCACCTGT | | | | | 1642 |
| Pro | Glu | Ala | Lys | Ala | Ile | Ser | | | | | | | | | | |
| | | | | 520 | | | | | | | | | | | | |

```
GTGACGCTGC CTTTTTATAC ACTGTCCTCC TCCACCTTGA TGGACCCCTA GTGATGCATC    1702
CTGCCTAGGC TGGACTTAAC CCCTTCCTCC NTGTCCCCAC GACCAACTGT CCCCAGTTAC    1762
TCTAACCGTT ATTTCATTTA GCTNCCATAT ATATTTTCTT ACCTAAGAGA ATAGTTTCCT    1822
GCTTTAAGNA AAAGACCTAC AATAGGTGGT GGAATTATGG GATGGGGTGG AGTATTGATA    1882
TAAATATATA AATACAAATG TATATTTTTC AGGATGTGGT TTAGGAACTG GGAATAACGT    1942
TTTCATGGCA CCATCAGGAG TAACAGAAAA CC                                  1974
```

(2) INFORMATION FOR SEQ ID NO:2:

(i) SEQUENCE CHARACTERISTICS:
        (A) LENGTH: 522 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ser Gly Gly Gly Gly Cys Ser Ala Ser Glu Arg Leu Pro Pro
 1               5                  10                  15

Pro Phe Pro Gly Leu Glu Pro Glu Ser Glu Gly Ala Ala Gly Gly Ser
                20                  25                  30

Glu Pro Glu Ala Gly Asp Ser Asp Thr Gly Glu Gly Glu Asp Ile Phe Thr
                35              40                  45

Gly Ala Ala Val Val Ser Lys His Gln Ser Pro Lys Ile Thr Thr Ser
     50                  55                  60

Leu Leu Pro Ile Asn Asn Gly Ser Lys Glu Asn Gly Ile His Glu Glu
 65                  70                  75                  80

Gln Asp Gln Glu Pro Gln Asp Leu Phe Ala Asp Ala Thr Val Glu Leu
                85                  90                  95

Ser Leu Asp Ser Thr Gln Asn Asn Gln Lys Lys Val Leu Ala Lys Thr
                100                 105                 110

Leu Ile Xaa Leu Pro Pro Gln Glu Ala Thr Asn Ser Ser Lys Pro Gln
            115                 120                 125

Pro Thr Tyr Glu Glu Leu Glu Glu Glu Gln Glu Asp Gln Phe Asp
        130                 135                 140

Leu Thr Val Gly Ile Thr Asp Pro Glu Lys Ile Gly Asp Gly Met Asn
145                 150                 155                 160

Ala Tyr Val Ala Tyr Lys Val Thr Thr Gln Thr Ser Leu Pro Leu Phe
                165                 170                 175

Arg Ser Lys Gln Phe Ala Val Lys Arg Arg Phe Ser Asp Phe Leu Gly
            180                 185                 190

Leu Tyr Glu Lys Leu Ser Glu Lys His Ser Gln Asn Gly Phe Ile Val
        195                 200                 205

Pro Pro Pro Pro Glu Lys Ser Leu Ile Gly Met Thr Lys Val Lys Val
```

|  |  |  |  | 210 |  |  |  |  | 215 |  |  |  |  | 220 |  |
|---|---|---|---|---|---|---|---|---|---|---|---|---|---|---|---|
| Gly | Lys | Glu | Asp | Ser | Ser | Ser | Ala | Glu | Phe | Leu | Glu | Lys | Arg | Arg | Ala |
| 225 |  |  |  |  | 230 |  |  |  | 235 |  |  |  |  |  | 240 |
| Ala | Leu | Glu | Arg | Tyr | Leu | Gln | Arg | Ile | Val | Asn | His | Pro | Thr | Met | Leu |
|  |  |  |  | 245 |  |  |  |  | 250 |  |  |  |  | 255 |  |
| Gln | Asp | Pro | Asp | Val | Arg | Glu | Phe | Leu | Glu | Lys | Glu | Glu | Leu | Pro | Arg |
|  |  |  | 260 |  |  |  |  | 265 |  |  |  |  | 270 |  |  |
| Ala | Val | Gly | Thr | Gln | Thr | Leu | Ser | Gly | Ala | Gly | Leu | Leu | Lys | Met | Phe |
|  |  | 275 |  |  |  |  | 280 |  |  |  |  | 285 |  |  |  |
| Asn | Lys | Ala | Thr | Asp | Ala | Val | Ser | Lys | Met | Thr | Ile | Lys | Met | Asn | Glu |
|  | 290 |  |  |  |  | 295 |  |  |  |  | 300 |  |  |  |  |
| Ser | Asp | Ile | Trp | Phe | Glu | Glu | Lys | Leu | Gln | Glu | Val | Glu | Cys | Glu | Glu |
| 305 |  |  |  |  | 310 |  |  |  | 315 |  |  |  |  |  | 320 |
| Gln | Arg | Leu | Arg | Lys | Leu | His | Ala | Val | Val | Glu | Thr | Leu | Val | Asn | His |
|  |  |  |  | 325 |  |  |  |  | 330 |  |  |  |  | 335 |  |
| Arg | Lys | Glu | Leu | Ala | Leu | Asn | Thr | Ala | Gln | Phe | Ala | Lys | Ser | Leu | Ala |
|  |  |  | 340 |  |  |  |  | 345 |  |  |  |  | 350 |  |  |
| Met | Leu | Gly | Ser | Ser | Glu | Asp | Asn | Thr | Ala | Leu | Ser | Arg | Ala | Leu | Ser |
|  |  | 355 |  |  |  |  | 360 |  |  |  |  | 365 |  |  |  |
| Gln | Leu | Ala | Glu | Val | Glu | Glu | Lys | Ile | Glu | Gln | Leu | His | Gln | Glu | Gln |
|  | 370 |  |  |  |  | 375 |  |  |  |  | 380 |  |  |  |  |
| Ala | Asn | Asn | Asp | Phe | Phe | Leu | Leu | Ala | Glu | Leu | Leu | Ser | Asp | Tyr | Ile |
| 385 |  |  |  |  | 390 |  |  |  | 395 |  |  |  |  |  | 400 |
| Arg | Leu | Leu | Ala | Ile | Val | Arg | Ala | Ala | Phe | Asp | Gln | Arg | Met | Lys | Thr |
|  |  |  |  | 405 |  |  |  |  | 410 |  |  |  |  | 415 |  |
| Trp | Gln | Arg | Trp | Gln | Asp | Ala | Gln | Ala | Thr | Leu | Gln | Lys | Lys | Arg | Glu |
|  |  |  | 420 |  |  |  |  | 425 |  |  |  |  | 430 |  |  |
| Ala | Glu | Ala | Arg | Leu | Leu | Trp | Ala | Asn | Lys | Pro | Asp | Lys | Leu | Gln | Gln |
|  |  | 435 |  |  |  |  | 440 |  |  |  |  | 445 |  |  |  |
| Ala | Lys | Asp | Glu | Ile | Leu | Glu | Trp | Glu | Ser | Arg | Val | Thr | Gln | Tyr | Glu |
|  | 450 |  |  |  |  | 455 |  |  |  |  | 460 |  |  |  |  |
| Arg | Asp | Phe | Glu | Arg | Ile | Ser | Thr | Val | Val | Arg | Lys | Glu | Val | Ile | Arg |
| 465 |  |  |  |  | 470 |  |  |  | 475 |  |  |  |  |  | 480 |
| Phe | Glu | Lys | Glu | Lys | Ser | Lys | Asp | Phe | Lys | Asn | His | Val | Ile | Lys | Tyr |
|  |  |  |  | 485 |  |  |  |  | 490 |  |  |  |  | 495 |  |
| Leu | Glu | Thr | Leu | Leu | Tyr | Ser | Gln | Gln | Gln | Leu | Ala | Lys | Tyr | Trp | Glu |
|  |  |  | 500 |  |  |  |  | 505 |  |  |  |  | 510 |  |  |
| Ala | Phe | Leu | Pro | Glu | Ala | Lys | Ala | Ile | Ser |  |  |  |  |  |  |
|  |  | 515 |  |  |  |  | 520 |  |  |  |  |  |  |  |  |

( 2 ) INFORMATION FOR SEQ ID NO:3:

( i ) SEQUENCE CHARACTERISTICS:
        ( A ) LENGTH: 1353 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..1353

( x i ) SEQUENCE DESCRIPTION: SEQ ID NO:3:

| ATG | GAT | GAC | AGA | GAA | GAT | CTT | TTT | GCA | GAA | GCC | ACA | GAA | GAA | GTA | TCT | 48 |
|---|---|---|---|---|---|---|---|---|---|---|---|---|---|---|---|---|
| Met | Asp | Asp | Arg | Glu | Asp | Leu | Phe | Ala | Glu | Ala | Thr | Glu | Glu | Val | Ser |  |
| 1 |  |  |  | 5 |  |  |  |  | 10 |  |  |  |  | 15 |  |  |
| TTG | GAC | GGC | CTG | AAA | GGG | AAC | CTC | TCC | TAT | CCT | CGG | AAC | CTT | CCC | CTG | 96 |
| Leu | Asp | Gly | Leu | Lys | Gly | Asn | Leu | Ser | Tyr | Pro | Arg | Asn | Leu | Pro | Leu |  |

|   |   |   |   |   | 20 |   |   |   |   | 25 |   |   |   |   | 30 |   |   |   |
|---|---|---|---|---|---|---|---|---|---|---|---|---|---|---|---|---|---|---|
| CAG | TCA | CAC | CTG | TCA | CTC | CTA | CTA | CAC | TCT | GCT | CCT | AGA | ATT | GAA | TCA | | | 144 |
| Gln | Ser | His | Leu | Ser | Leu | Leu | Leu | His | Ser | Ala | Pro | Arg | Ile | Glu | Ser | | | |
| | | 35 | | | | | 40 | | | | | 45 | | | | | | |
| AAG | AGT | ATG | TCT | GCT | CCC | GTG | ATC | TTT | GAT | AGA | TCC | AGG | GAA | GAG | ATT | | | 192 |
| Lys | Ser | Met | Ser | Ala | Pro | Val | Ile | Phe | Asp | Arg | Ser | Arg | Glu | Glu | Ile | | | |
| | 50 | | | | | 55 | | | | | 60 | | | | | | | |
| GAA | GAA | GAA | GCA | AAT | GGA | GAC | ATT | TTT | GAC | ATA | GAA | ATT | GGT | GTA | TCA | | | 240 |
| Glu | Glu | Glu | Ala | Asn | Gly | Asp | Ile | Phe | Asp | Ile | Glu | Ile | Gly | Val | Ser | | | |
| 65 | | | | | 70 | | | | | 75 | | | | | 80 | | | |
| GAT | CCA | GAA | AAA | GTT | GGT | GAT | GGC | ATG | AAT | GCC | TAT | ATG | GCA | TAT | AGA | | | 288 |
| Asp | Pro | Glu | Lys | Val | Gly | Asp | Gly | Met | Asn | Ala | Tyr | Met | Ala | Tyr | Arg | | | |
| | | | | 85 | | | | | 90 | | | | | 95 | | | | |
| GTA | ACA | ACA | AAG | ACA | TCT | CTT | TCC | ATG | TTC | AGT | AAG | AGT | GAA | TTT | TCA | | | 336 |
| Val | Thr | Thr | Lys | Thr | Ser | Leu | Ser | Met | Phe | Ser | Lys | Ser | Glu | Phe | Ser | | | |
| | | | 100 | | | | | 105 | | | | | 110 | | | | | |
| GTG | AAA | AGA | TTC | ACC | GAC | TTT | CTT | GGT | TTG | CAC | ACC | ACA | TTA | CCA | ACC | | | 384 |
| Val | Lys | Arg | Phe | Thr | Asp | Phe | Leu | Gly | Leu | His | Thr | Thr | Leu | Pro | Thr | | | |
| | | 115 | | | | | 120 | | | | | 125 | | | | | | |
| ACA | TAT | TTA | CAT | GTT | GTT | ATA | TTT | GTT | GCC | ACC | AGC | TCC | AGA | AAG | AGT | | | 432 |
| Thr | Tyr | Leu | His | Val | Val | Ile | Phe | Val | Ala | Thr | Ser | Ser | Arg | Lys | Ser | | | |
| | | 130 | | | | | 135 | | | | | 140 | | | | | | |
| ATA | GTA | GGG | ATG | ACC | AAG | GTC | AAA | GTG | GGT | AAA | GAA | GAC | TCA | TCA | TCC | | | 480 |
| Ile | Val | Gly | Met | Thr | Lys | Val | Lys | Val | Gly | Lys | Glu | Asp | Ser | Ser | Ser | | | |
| 145 | | | | | 150 | | | | | 155 | | | | | 160 | | | |
| ACT | GAG | TTT | GTA | GAA | AAA | CGG | AGA | GCA | GCT | CTT | GAA | AGG | TAT | CTT | CAA | | | 528 |
| Thr | Glu | Phe | Val | Glu | Lys | Arg | Arg | Ala | Ala | Leu | Glu | Arg | Tyr | Leu | Gln | | | |
| | | | | 165 | | | | | 170 | | | | | 175 | | | | |
| AGA | ACA | GTA | AAA | CAT | CCA | ACT | TTA | CTA | CAG | GAT | CCT | GAT | TTA | AGG | CAG | | | 576 |
| Arg | Thr | Val | Lys | His | Pro | Thr | Leu | Leu | Gln | Asp | Pro | Asp | Leu | Arg | Gln | | | |
| | | | 180 | | | | | 185 | | | | | 190 | | | | | |
| TTC | TTG | GAA | AGT | TCA | GAG | CTG | CCT | AGA | GCA | GTT | AAT | ACA | CAG | GCT | CTG | | | 624 |
| Phe | Leu | Glu | Ser | Ser | Glu | Leu | Pro | Arg | Ala | Val | Asn | Thr | Gln | Ala | Leu | | | |
| | | | 195 | | | | | 200 | | | | | 205 | | | | | |
| AGT | GGA | GCT | GGA | ATA | TTG | AGG | ATG | GTG | AAC | AAG | GCT | GCC | GAC | GCT | GTC | | | 672 |
| Ser | Gly | Ala | Gly | Ile | Leu | Arg | Met | Val | Asn | Lys | Ala | Ala | Asp | Ala | Val | | | |
| | 210 | | | | | 215 | | | | | 220 | | | | | | | |
| AAC | AAA | ATG | ACA | ATC | AAG | ATG | AAT | GAA | TCG | GAT | GCA | TGG | TTT | GAA | GAA | | | 720 |
| Asn | Lys | Met | Thr | Ile | Lys | Met | Asn | Glu | Ser | Asp | Ala | Trp | Phe | Glu | Glu | | | |
| 225 | | | | | 230 | | | | | 235 | | | | | 240 | | | |
| AAG | CAG | CAG | CAA | TTT | GAG | AAT | CTG | GAT | CAG | CAA | CTT | AGG | AAA | CTT | CAT | | | 768 |
| Lys | Gln | Gln | Gln | Phe | Glu | Asn | Leu | Asp | Gln | Gln | Leu | Arg | Lys | Leu | His | | | |
| | | | | 245 | | | | | 250 | | | | | 255 | | | | |
| GTC | AGT | GTT | GAA | GCC | TTG | GTC | TGT | CAT | AGA | AAA | GAA | CTT | TCA | GCC | AAC | | | 816 |
| Val | Ser | Val | Glu | Ala | Leu | Val | Cys | His | Arg | Lys | Glu | Leu | Ser | Ala | Asn | | | |
| | | | 260 | | | | | 265 | | | | | 270 | | | | | |
| ACA | GCT | GCC | TTT | GCT | AAA | AGT | GCT | GCC | ATG | TTA | GGT | AAT | TCT | GAG | GAT | | | 864 |
| Thr | Ala | Ala | Phe | Ala | Lys | Ser | Ala | Ala | Met | Leu | Gly | Asn | Ser | Glu | Asp | | | |
| | | 275 | | | | | 280 | | | | | 285 | | | | | | |
| CAT | ACT | GCT | TTA | TCT | AGA | GCT | TTG | TCT | CAG | CTT | GCA | GAG | GTT | GAG | GAG | | | 912 |
| His | Thr | Ala | Leu | Ser | Arg | Ala | Leu | Ser | Gln | Leu | Ala | Glu | Val | Glu | Glu | | | |
| | | 290 | | | | | 295 | | | | | 300 | | | | | | |
| AAG | ATA | GAC | CAG | TTA | CAT | CAA | GAA | CAA | GCT | TTT | GCT | GAC | TTT | TAT | ATG | | | 960 |
| Lys | Ile | Asp | Gln | Leu | His | Gln | Glu | Gln | Ala | Phe | Ala | Asp | Phe | Tyr | Met | | | |
| 305 | | | | | 310 | | | | | 315 | | | | | 320 | | | |
| TTC | TCA | GAA | CTA | CTT | AGT | GAC | TAC | ATT | CGT | CTT | ATT | GCT | GCA | GTG | AAA | | | 1008 |
| Phe | Ser | Glu | Leu | Leu | Ser | Asp | Tyr | Ile | Arg | Leu | Ile | Ala | Ala | Val | Lys | | | |
| | | | | 325 | | | | | 330 | | | | | 335 | | | | |
| GGT | GTG | TTT | GAC | CAT | CGA | ATG | AAG | TGC | TGG | CAG | AAA | TGG | GAA | GAT | GCT | | | 1056 |
| Gly | Val | Phe | Asp | His | Arg | Met | Lys | Cys | Trp | Gln | Lys | Trp | Glu | Asp | Ala | | | |

```
                        340                           345                            350
CAA  ATT  ACT  TTG  CTC  AAA  AAA  CGT  GAA  GCT  GAA  GCA  AAA  ATG  ATG  GTT       1104
Gln  Ile  Thr  Leu  Leu  Lys  Lys  Arg  Glu  Ala  Glu  Ala  Lys  Met  Met  Val
          355                           360                      365

GCT  AAC  AAA  CCA  GAT  AAA  ATA  CAG  CAA  GCT  AAA  AAT  GAA  ATA  AGA  GAG       1152
Ala  Asn  Lys  Pro  Asp  Lys  Ile  Gln  Gln  Ala  Lys  Asn  Glu  Ile  Arg  Glu
     370                      375                           380

TGG  GAG  GCG  AAA  GTG  CAA  CAA  GGG  GAA  AGA  GAT  TTT  GAA  CAG  ATA  TCT       1200
Trp  Glu  Ala  Lys  Val  Gln  Gln  Gly  Glu  Arg  Asp  Phe  Glu  Gln  Ile  Ser
385                 390                      395                           400

AAA  ACG  ATT  CGA  AAA  GAA  GTG  GGA  AGA  TTT  GAG  AAA  GAA  CGA  GTG  AAG       1248
Lys  Thr  Ile  Arg  Lys  Glu  Val  Gly  Arg  Phe  Glu  Lys  Glu  Arg  Val  Lys
               405                      410                      415

GAT  TTT  AAA  ACC  GTT  ATC  ATC  AAG  TAC  TTA  GAA  TCA  CTA  GTT  CAA  ACA       1296
Asp  Phe  Lys  Thr  Val  Ile  Ile  Lys  Tyr  Leu  Glu  Ser  Leu  Val  Gln  Thr
               420                      425                      430

CAA  CAA  CAG  CTG  ATA  AAA  TAC  TGG  GAA  GCA  TTC  CTA  CCT  GAA  GCC  AAA       1344
Gln  Gln  Gln  Leu  Ile  Lys  Tyr  Trp  Glu  Ala  Phe  Leu  Pro  Glu  Ala  Lys
          435                      440                      445

GCC  ATT  GCC                                                                         1353
Ala  Ile  Ala
          450
```

( 2 ) INFORMATION FOR SEQ ID NO:4:

( i ) SEQUENCE CHARACTERISTICS:
        ( A ) LENGTH: 451 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Asp  Asp  Arg  Glu  Asp  Leu  Phe  Ala  Glu  Ala  Thr  Glu  Glu  Val  Ser
 1                  5                        10                       15

Leu  Asp  Gly  Leu  Lys  Gly  Asn  Leu  Ser  Tyr  Pro  Arg  Asn  Leu  Pro  Leu
               20                       25                       30

Gln  Ser  His  Leu  Ser  Leu  Leu  Leu  His  Ser  Ala  Pro  Arg  Ile  Glu  Ser
               35                       40                       45

Lys  Ser  Met  Ser  Ala  Pro  Val  Ile  Phe  Asp  Arg  Ser  Arg  Glu  Glu  Ile
          50                       55                       60

Glu  Glu  Glu  Ala  Asn  Gly  Asp  Ile  Phe  Asp  Ile  Glu  Ile  Gly  Val  Ser
 65                      70                       75                       80

Asp  Pro  Glu  Lys  Val  Gly  Asp  Gly  Met  Asn  Ala  Tyr  Met  Ala  Tyr  Arg
               85                       90                       95

Val  Thr  Thr  Lys  Thr  Ser  Leu  Ser  Met  Phe  Ser  Lys  Ser  Glu  Phe  Ser
               100                      105                      110

Val  Lys  Arg  Phe  Thr  Asp  Phe  Leu  Gly  Leu  His  Thr  Thr  Leu  Pro  Thr
          115                      120                      125

Thr  Tyr  Leu  His  Val  Val  Ile  Phe  Val  Ala  Thr  Ser  Ser  Arg  Lys  Ser
          130                      135                      140

Ile  Val  Gly  Met  Thr  Lys  Val  Lys  Val  Gly  Lys  Glu  Asp  Ser  Ser  Ser
145                      150                      155                      160

Thr  Glu  Phe  Val  Glu  Lys  Arg  Ala  Ala  Leu  Glu  Arg  Tyr  Leu  Gln
               165                      170                      175

Arg  Thr  Val  Lys  His  Pro  Thr  Leu  Leu  Gln  Asp  Pro  Asp  Leu  Arg  Gln
               180                      185                      190

Phe  Leu  Glu  Ser  Ser  Glu  Leu  Pro  Arg  Ala  Val  Asn  Thr  Gln  Ala  Leu
               195                      200                      205
```

```
Ser  Gly  Ala  Gly  Ile  Leu  Arg  Met  Val  Asn  Lys  Ala  Ala  Asp  Ala  Val
     210                      215                 220

Asn  Lys  Met  Thr  Ile  Lys  Met  Asn  Glu  Ser  Asp  Ala  Trp  Phe  Glu  Glu
225                           230                 235                      240

Lys  Gln  Gln  Gln  Phe  Glu  Asn  Leu  Asp  Gln  Gln  Leu  Arg  Lys  Leu  His
               245                      250                           255

Val  Ser  Val  Glu  Ala  Leu  Val  Cys  His  Arg  Lys  Glu  Leu  Ser  Ala  Asn
               260                 265                      270

Thr  Ala  Ala  Phe  Ala  Lys  Ser  Ala  Ala  Met  Leu  Gly  Asn  Ser  Glu  Asp
          275                      280                      285

His  Thr  Ala  Leu  Ser  Arg  Ala  Leu  Ser  Gln  Leu  Ala  Glu  Val  Glu  Glu
     290                      295                      300

Lys  Ile  Asp  Gln  Leu  His  Gln  Glu  Gln  Ala  Phe  Ala  Asp  Phe  Tyr  Met
305                      310                      315                      320

Phe  Ser  Glu  Leu  Leu  Ser  Asp  Tyr  Ile  Arg  Leu  Ile  Ala  Ala  Val  Lys
                    325                      330                      335

Gly  Val  Phe  Asp  His  Arg  Met  Lys  Cys  Trp  Gln  Lys  Trp  Glu  Asp  Ala
               340                 345                      350

Gln  Ile  Thr  Leu  Leu  Lys  Lys  Arg  Glu  Ala  Glu  Ala  Lys  Met  Met  Val
          355                      360                      365

Ala  Asn  Lys  Pro  Asp  Lys  Ile  Gln  Gln  Ala  Lys  Asn  Glu  Ile  Arg  Glu
     370                      375                 380

Trp  Glu  Ala  Lys  Val  Gln  Gln  Gly  Glu  Arg  Asp  Phe  Glu  Gln  Ile  Ser
385                      390                 395                           400

Lys  Thr  Ile  Arg  Lys  Glu  Val  Gly  Arg  Phe  Glu  Lys  Glu  Arg  Val  Lys
               405                      410                           415

Asp  Phe  Lys  Thr  Val  Ile  Ile  Lys  Tyr  Leu  Glu  Ser  Leu  Val  Gln  Thr
               420                      425                      430

Gln  Gln  Gln  Leu  Ile  Lys  Tyr  Trp  Glu  Ala  Phe  Leu  Pro  Glu  Ala  Lys
               435                      440                 445

Ala  Ile  Ala
     450
```

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:5:

Tyr  Leu  Val  Ile
    1

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:6:

Phe  Val  Val  Ile
    1

( 2 ) INFORMATION FOR SEQ ID NO:7:

( i ) SEQUENCE CHARACTERISTICS:
        ( A ) LENGTH: 15 amino acids ( B ) TYPE: amino acid
( D ) TOPOLOGY: linear ( x i ) SEQUENCE DESCRIPTION: SEQ ID NO:7:

Cys Lys Tyr Leu Glu Ala Phe Leu Pro Glu Ala Lys Ala Ile Ser
1               5                   10                  15

( 2 ) INFORMATION FOR SEQ ID NO:8:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:8:

GATCCGTCGA CGGGAGCTTG TGGAGCCTCT TACA                                34

( 2 ) INFORMATION FOR SEQ ID NO:9:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:9:

GGCTGCAGGT CGACTGAATG ACAAGGTAGC GCTG                                34

( 2 ) INFORMATION FOR SEQ ID NO:10:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:10:

GATGTTAACG ATACCAGCCT CTTGCTGAGT                                     30

( 2 ) INFORMATION FOR SEQ ID NO:11:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:11:

CTTTCTCAAA CCTCACTTCT                                                20

( 2 ) INFORMATION FOR SEQ ID NO:12:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:12:

TTGCTTCAGC TTCACGTTTT TTGAGCAA                                       28

( 2 ) INFORMATION FOR SEQ ID NO:13:

( i ) SEQUENCE CHARACTERISTICS:
( A ) LENGTH: 27 base pairs
( B ) TYPE: nucleic acid
( C ) STRANDEDNESS: single (D) TOPOLOGY: linear (xi) SEQUENCE DESCRIPTION: SEQ ID NO:13:

TGACCATCGA ATGAAGTGCT GGCAGAA  27

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:14:

GATCCGTCGA CGGGAGCTTG TGGAGCCTCT TACA  34

(2) INFORMATION FOR SEQ ID NO:15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:15:

GGCTGCAGGT CGACTGAATG ACAAGGTAGC GCTG  34

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:16:

GATCCCATGG CGCCACATCG TTCGGAAGCG  30

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:17:

CCCCTCGAGG TCGACGGTAT CGATAAGCTT  30

(2) INFORMATION FOR SEQ ID NO:18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:18:

GATCCTCGAG GATGATCAAC TCACGGAACT T  31

(2) INFORMATION FOR SEQ ID NO:19:

(i) SEQUENCE CHARACTERISTICS:
        (A) LENGTH: 31 base pairs
        (B) TYPE: nucleic acid
        (C) STRANDEDNESS: single
        (D) TOPOLOGY: linear ( x i ) SEQUENCE DESCRIPTION: SEQ ID NO:19:

GATCCGTCGA CGGCAGAAGA TCCGGAAGTA T 31

( 2 ) INFORMATION FOR SEQ ID NO:20:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:20:

GGCTGCAGGT CGACGGTACT GTCCATGGGG CTGGA 35

( 2 ) INFORMATION FOR SEQ ID NO:21:

( i ) SEQUENCE CHARACTERISTICS:
( A ) LENGTH: 48 amino acids
( B ) TYPE: amino acid
( D ) TOPOLOGY: linear ( x i ) SEQUENCE DESCRIPTION: SEQ ID NO:21:

Phe Arg Glu Leu Ile Ile Glu Phe Ser Lys Met Ala Arg Asp Pro Gln
1               5                   10                  15

Arg Tyr Leu Val Ile Gln Gly Asp Glu Arg Met His Leu Pro Ser Pro
            20                  25                  30

Thr Asp Ser Asn Phe Tyr Arg Ala Leu Met Asp Glu Asp Met Asp
        35                  40                  45

( 2 ) INFORMATION FOR SEQ ID NO:22:

( i ) SEQUENCE CHARACTERISTICS:
( A ) LENGTH: 47 amino acids
( B ) TYPE: amino acid
( D ) TOPOLOGY: linear ( x i ) SEQUENCE DESCRIPTION: SEQ ID NO:22:

Phe Arg Glu Leu Val Ser Glu Phe Ser Arg Met Ala Arg Asp Pro Gln
1               5                   10                  15

Arg Phe Val Val Ile Gln Asn Glu Asp Leu Gly Pro Ala Ser Pro Leu
            20                  25                  30

Asp Ser Thr Phe Tyr Arg Ser Leu Leu Glu Asp Asp Met Gly
        35                  40                  45

( 2 ) INFORMATION FOR SEQ ID NO:23:

( i ) SEQUENCE CHARACTERISTICS:
( A ) LENGTH: 47 amino acids
( B ) TYPE: amino acid
( D ) TOPOLOGY: linear ( x i ) SEQUENCE DESCRIPTION: SEQ ID NO:23:

Phe Arg Glu Leu Val Ser Glu Phe Ser Arg Met Ala Arg Asp Pro Gln
1               5                   10                  15

Arg Phe Val Val Ile Gln Asn Glu Asp Leu Gly Pro Ser Ser Pro Met
            20                  25                  30

Asp Ser Thr Phe Tyr Arg Ser Leu Leu Glu Asp Asp Met Gly
        35                  40                  45

( 2 ) INFORMATION FOR SEQ ID NO:24:

( i ) SEQUENCE CHARACTERISTICS:
( A ) LENGTH: 48 amino acids
( B ) TYPE: amino acid (D) TOPOLOGY: linear (xi) SEQUENCE DESCRIPTION: SEQ ID NO:24:

| Phe | Lys | Glu | Leu | Ala | Asn | Glu | Phe | Thr | Arg | Met | Ala | Arg | Asp | Pro | Pro |
|---|---|---|---|---|---|---|---|---|---|---|---|---|---|---|---|
| 1 | | | | 5 | | | | | 10 | | | | | 15 | |
| Arg | Tyr | Leu | Val | Ile | Lys | Arg | Glu | Ser | Gly | Pro | Gly | Ile | Ala | Pro | Gly |
| | | | 20 | | | | | 25 | | | | | 30 | | |
| Pro | Glu | Pro | His | Gly | Leu | Thr | Asn | Lys | Lys | Leu | Glu | Glu | Val | Glu | Leu |
| | | 35 | | | | | 40 | | | | | 45 | | | |

(2) INFORMATION FOR SEQ ID NO:25:

(i) SEQUENCE CHARACTERISTICS:
  (A) LENGTH: 48 amino acids
  (B) TYPE: amino acid
  (D) TOPOLOGY: linear (xi) SEQUENCE DESCRIPTION: SEQ ID NO:25:

| Phe | Lys | Glu | Leu | Ala | Ala | Glu | Phe | Ser | Arg | Met | Ala | Arg | Asp | Pro | Gln |
|---|---|---|---|---|---|---|---|---|---|---|---|---|---|---|---|
| 1 | | | | 5 | | | | | 10 | | | | | 15 | |
| Arg | Tyr | Leu | Val | Ile | Gln | Gly | Asp | Asp | Arg | Met | Lys | Leu | Pro | Ser | Pro |
| | | | 20 | | | | | 25 | | | | | 30 | | |
| Asn | Asp | Ser | Lys | Phe | Phe | Gln | Asn | Leu | Leu | Asp | Glu | Glu | Asp | Leu | Glu |
| | | 35 | | | | | 40 | | | | | 45 | | | |

We claim:

1. A substantially purified nucleic acid molecule encoding a sorting nexin (SNX), said SNX having the ability to bind an intracellular domain of an activated cell surface receptor expressed on a cell and direct translocation of the receptor to a lysosome in the cell.

2. The substantially purified nucleic acid molecule of claim 1 having the nucleotide sequence shown as SEQ ID NO: 1.

3. The substantially purified nucleic acid molecule of claim 1 encoding the amino acid sequence shown as SEQ ID NO: 2.

4. The substantially purified nucleic acid molecule of claim 1 having the nucleotide sequence shown as SEQ ID NO: 3.

5. The substantially purified nucleic acid molecule of claim 1 encoding the amino acid sequence shown as SEQ ID NO: 4.

6. The substantially purified nucleic acid molecule of claim 1 encoding the amino acid sequence shown as amino acids 93 to 452 of SEQ ID NO: 4.

7. A substantially purified nucleic acid molecule encoding a peptide fragment of a polypeptide selected from the group consisting of the amino acid sequence shown as SEQ ID NO: 2 and the amino acid sequence shown as SEQ ID NO: 4, said fragment having the ability to bind an intracellular domain of an activated cell surface receptor expressed on a cell and direct the translocation of the receptor to a lysosome in the cell.

8. The substantially purified nucleic acid molecule of claim 1, said peptide fragment having an amino acid sequence selected from the group consisting of the amino acid sequences shown as amino acids 214 to 265 in SEQ ID NO: 2; amino acids 465 to 522 in SEQ ID NO: 2; amino acids 143 to 194 in SEQ ID NO: 4; and amino acids 394 to 452 in SEQ ID NO: 4.

9. A substantially purified nucleic acid molecule, said nucleic acid molecule being complementary to the nucleic acid molecule of claim 1.

10. A vector comprising the nucleic acid molecule of claim 1.

11. The vector of claim 10, wherein said vector is an expression vector.

12. A host cell containing the vector of claim 10.

13. A method of down regulating the expression of a receptor expressed on the surface of a cell, comprising the steps of:
  a. introducing the nucleic acid molecule of claim 1 into the cell; and
  b. expressing the SNX encoded by said nucleic acid molecule, wherein said SNX binds the intracelluar domain of the activated cell surface receptor expressed on the surface of the cell and down regulates the expression of the receptor.

14. The method of claim 13, wherein said receptor is a growth factor receptor.

15. The method of claim 14, wherein said growth factor receptor is an epidermal growth factor receptor.

16. The method of claim 13, wherein said SNX (SEQ ID NO: 2) is SNX1.

17. The method of claim 13, wherein said SNX (SEQ ID NO: 4) is SNX2.

* * * * *